US010993682B2

(12) United States Patent
Nabeta et al.

(10) Patent No.: US 10,993,682 B2
(45) Date of Patent: May 4, 2021

(54) RADIOGRAPHIC IMAGING APPARATUS COMPRISING A LEG UNIT HAVING THREE OR MORE WHEEL UNITS

(71) Applicant: FUJIFILM Corporation, Tokyo (JP)

(72) Inventors: Toshiyuki Nabeta, Kanagawa (JP);
Ryosuke Ogura, Kanagawa (JP);
Masayoshi Matsuura, Kanagawa (JP);
Fumito Nariyuki, Kanagawa (JP);
Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 348 days.

(21) Appl. No.: 15/864,041

(22) Filed: Jan. 8, 2018

(65) Prior Publication Data

US 2018/0125439 A1    May 10, 2018

Related U.S. Application Data

(63) Continuation of application No. PCT/JP2016/002483, filed on May 23, 2016.

(30) Foreign Application Priority Data

Jul. 16, 2015  (JP) .............................. JP2015-141787

(51) Int. Cl.
*A61B 6/00* (2006.01)
*B60B 33/00* (2006.01)
*G01T 1/161* (2006.01)

(52) U.S. Cl.
CPC .............. *A61B 6/4405* (2013.01); *A61B 6/42* (2013.01); *A61B 6/4208* (2013.01);
(Continued)

(58) Field of Classification Search
CPC ....... A61B 6/42; A61B 6/4208; A61B 6/4283; A61B 6/44; A61B 6/4405; A61B 6/4411;
(Continued)

(56) References Cited

U.S. PATENT DOCUMENTS 5,143,333 A    9/1992  Warden
5,283,823 A *  2/1994  Morris ................. A61B 6/4405
                                              378/193

(Continued)

FOREIGN PATENT DOCUMENTS

CN    102481132 A    5/2012
CN    104068874 A    10/2014
(Continued)

OTHER PUBLICATIONS

Communication dated May 23, 2018, from the European Patent Office in counterpart application No. 16824019.0.
(Continued)

*Primary Examiner* — Allen C. Ho
(74) *Attorney, Agent, or Firm* — Sughrue Mion, PLLC

(57) ABSTRACT

A radiographic imaging apparatus in which a radiation source support unit supports a radiation source is adapted to be capable of being quickly carried to a use position in a small radius. A radiographic imaging apparatus includes a leg unit that includes three or more wheel units and is capable of traveling on an apparatus-placement surface by using wheels, a body unit that is held on the leg unit, an arm unit as a radiation source support unit that is connected to the body unit, a radiation source that is mounted on the arm unit, a battery that is received in the body unit and drives the radiation source, and a circuit that is received in the body unit and relates to the drive of the radiation source. The wheel unit is formed of a revolving caster.

17 Claims, 20 Drawing Sheets

(52) U.S. Cl.
CPC .............. *A61B 6/4283* (2013.01); *A61B 6/44* (2013.01); *A61B 6/4411* (2013.01); *A61B 6/4429* (2013.01); *A61B 6/4452* (2013.01); *A61B 6/4458* (2013.01); *A61B 6/56* (2013.01); *B60B 33/0081* (2013.01); *G01T 1/161* (2013.01)

(58) Field of Classification Search
CPC .... A61B 6/4429; A61B 6/4452; A61B 6/4458
USPC ......................................... 378/189, 196–198
See application file for complete search history.

(56) References Cited

U.S. PATENT DOCUMENTS

| | | | | |
|---|---|---|---|---|
| 6,543,936 B2* | 4/2003 | Feldman | ............... | A61B 6/145 378/191 |
| 7,309,159 B2* | 12/2007 | Watanabe | ............... | A61B 6/10 378/117 |
| 7,810,994 B2* | 10/2010 | Ohmura | ............... | A61B 6/4405 378/196 |
| 8,177,430 B2* | 5/2012 | Bouvier | ............... | A61B 6/4405 378/198 |
| 8,376,612 B2* | 2/2013 | Takae | ............... | A61B 6/4283 378/198 |
| 8,419,276 B2* | 4/2013 | Oda | ............... | A61B 6/4283 378/198 |
| 8,459,868 B2* | 6/2013 | Boomgaarden | ...... | A61B 6/4405 378/198 |
| 8,568,028 B2* | 10/2013 | Wendlandt | ............. | A61B 6/447 378/193 |
| 8,636,410 B2* | 1/2014 | Yao | ............... | A61B 6/4405 378/197 |
| 8,662,536 B2* | 3/2014 | Moreno Vallejo | ...... | B62B 3/001 280/767 |
| 8,672,543 B2* | 3/2014 | Kralles | ............... | A61B 6/4405 378/102 |
| 8,705,699 B2* | 4/2014 | Fuse | ............... | A61B 6/4405 378/102 |
| 8,721,176 B2* | 5/2014 | McBroom | ............... | A61B 6/56 378/189 |
| 8,840,304 B2* | 9/2014 | Perez Zarate | ......... | A61B 6/4405 378/197 |
| 8,899,834 B2* | 12/2014 | Barker | ............... | A61B 6/4405 250/370.09 |
| 8,929,512 B2* | 1/2015 | Kamitake | ............... | A61B 6/00 378/102 |
| 8,961,011 B2* | 2/2015 | Lalena | ............... | A61B 6/465 378/198 |
| 8,998,487 B2* | 4/2015 | Watanabe | ............. | A61B 6/4405 378/193 |
| 9,022,650 B2* | 5/2015 | Kaku | ............... | H05G 1/02 378/102 |
| 9,044,191 B2* | 6/2015 | Nishino | ............... | A61B 6/4405 |
| 9,055,911 B2* | 6/2015 | Sakuragi | ............... | A61B 6/4405 |
| 9,060,741 B2* | 6/2015 | Fuse | ............... | A61B 6/542 |
| 9,078,597 B2* | 7/2015 | Patil | ............... | A61B 6/107 |
| 9,089,309 B2* | 7/2015 | Bouvier | ............... | A61B 6/547 |
| 9,101,316 B2* | 8/2015 | Liu | ............... | A61B 6/4233 |
| 9,101,319 B2* | 8/2015 | Kojima | ............... | A61B 6/4405 |
| 9,105,441 B2* | 8/2015 | Matsuda | ............... | H01J 35/16 |
| 9,121,805 B2* | 9/2015 | Omura | ............... | G01N 23/00 |
| 9,125,611 B2* | 9/2015 | Eaves | ............... | A61B 6/4405 |
| 9,131,592 B2* | 9/2015 | Kojima | ............... | A61B 6/4405 |
| 9,173,628 B2* | 11/2015 | Bouvier | ............... | A61B 6/4405 |
| 9,198,270 B2* | 11/2015 | Chicchetti | ............... | H05G 1/08 |
| 9,204,855 B2* | 12/2015 | Tsubota | ............... | H04W 76/10 |
| 9,259,203 B2* | 2/2016 | Bouvier | ............... | A61B 6/4405 |
| 9,275,770 B2* | 3/2016 | Omura | ............... | G21K 5/10 |
| 9,295,438 B2* | 3/2016 | Omura | ............... | A61B 6/4405 |
| 9,326,747 B2* | 5/2016 | Omura | ............... | A61B 6/4405 |
| 9,348,337 B2* | 5/2016 | Chen | ............... | A61B 6/102 |
| 9,364,188 B2* | 6/2016 | Okuno | ............... | A61B 6/105 |
| 9,380,988 B2* | 7/2016 | Kitano | ............... | A61B 6/4283 |
| 9,398,675 B2* | 7/2016 | Eaves | ............... | A61B 6/4233 |
| 9,398,885 B2* | 7/2016 | Suzuki | ............... | A61B 6/42 |
| 9,413,961 B2* | 8/2016 | Welsh | ............... | A61B 6/4405 |
| 9,414,794 B2* | 8/2016 | Kaku | ............... | A61B 6/4405 |
| 9,414,795 B2* | 8/2016 | Nakata | ............... | A61B 6/4405 |
| 9,414,802 B2* | 8/2016 | Urbon | ............... | A61B 6/4283 |
| 9,456,799 B2* | 10/2016 | Chicchetti | ............... | A61B 6/563 |
| 9,480,445 B2* | 11/2016 | Guldstrand | ............ | A61B 6/4405 |
| 9,492,137 B2* | 11/2016 | Iwamoto | ............... | A61B 6/4283 |
| 9,498,173 B2* | 11/2016 | Yamada | ............... | A61B 6/465 |
| 9,521,983 B2* | 12/2016 | Jang | ............... | A61B 6/4429 |
| 9,521,984 B2* | 12/2016 | Moreno Vallejo | ... | A61B 6/4405 |
| 9,538,978 B2* | 1/2017 | Makino | ............... | G16H 40/63 |
| 9,561,009 B2* | 2/2017 | Woudstra | ............. | A61B 6/4405 |
| 9,561,013 B2* | 2/2017 | Tsuchiya | ............... | A61B 6/4458 |
| 9,649,080 B2* | 5/2017 | Kwak | ............... | A61B 6/4429 |
| 9,655,575 B2* | 5/2017 | Park | ............... | A61B 6/4233 |
| 9,655,582 B2* | 5/2017 | Shirota | ............... | A61B 6/54 |
| 9,668,708 B2* | 6/2017 | Okuno | ............... | A61B 6/447 |
| 9,693,437 B2* | 6/2017 | Simmons | ............... | G01N 23/04 |
| 9,693,746 B2* | 7/2017 | Ancar | ............... | A61B 6/08 |
| 9,700,278 B2* | 7/2017 | Tezuka | ............... | A61B 6/563 |
| 9,730,653 B2* | 8/2017 | Niizeki | ............... | A61B 6/4405 |
| 9,743,894 B2* | 8/2017 | Okuno | ............... | A61B 6/4405 |
| 9,751,360 B2* | 9/2017 | Rijken | ............... | A61B 6/4405 |
| 9,848,841 B2* | 12/2017 | Choi | ............... | A61B 6/04 |
| 9,883,841 B2* | 2/2018 | Bååt | ............... | A61B 6/4283 |
| 9,931,089 B2* | 4/2018 | Nariyuki | ............... | A61B 6/107 |
| 9,936,931 B2* | 4/2018 | Adachi | ............... | A61B 6/04 |
| 10,010,301 B2* | 7/2018 | Katsumata | ............... | A61B 6/102 |
| 10,058,303 B2* | 8/2018 | Shimohira | ............... | A61B 6/06 |
| 10,064,588 B2* | 9/2018 | Uchida | ............... | A61B 6/4405 |
| 10,070,833 B2* | 9/2018 | Shirota | ............... | A61B 6/587 |
| 10,154,824 B2* | 12/2018 | Fortuna | ............... | A61B 6/447 |
| 10,219,764 B2* | 3/2019 | Yang | ............... | A61B 6/4405 |
| 10,219,766 B2* | 3/2019 | Park | ............... | A61B 6/4283 |
| 10,271,802 B2* | 4/2019 | Wendlandt | ............. | A61B 6/105 |
| 10,278,668 B2* | 5/2019 | Hishikawa | ........... | A61B 6/4405 |
| 10,292,673 B2* | 5/2019 | Niizeki | ............... | A61B 6/4405 |
| 10,368,816 B2* | 8/2019 | Bouvier | ............... | A61B 6/4441 |
| 10,433,805 B2* | 10/2019 | Hishida | ............... | A61B 6/06 |
| 10,456,100 B2* | 10/2019 | Ninomiya | ............ | A61B 6/4405 |
| 10,506,995 B2* | 12/2019 | Ninomiya | ............. | A61B 6/547 |
| 10,674,977 B2* | 6/2020 | Nabeta | ............... | A61B 6/4458 |
| 10,856,821 B2* | 12/2020 | Onobori et al. | ..... | A61B 6/4405 |
| 2002/0154742 A1 | 10/2002 | Feldman | | |
| 2010/0054422 A1 | 3/2010 | Ohmura et al. | | |
| 2010/0299014 A1 | 11/2010 | Bouvier | | |
| 2012/0148031 A1 | 6/2012 | Eaves | | |
| 2012/0155616 A1 | 6/2012 | Rijken et al. | | |
| 2013/0182828 A1 | 7/2013 | Watanabe et al. | | |
| 2014/0226795 A1 | 8/2014 | Kitano | | |
| 2014/0291555 A1 | 10/2014 | Sakuragi | | |

FOREIGN PATENT DOCUMENTS

| | | |
|---|---|---|
| EP | 2301440 A1 | 3/2011 |
| EP | 2506770 A1 | 10/2012 |
| JP | 03-99000 A | 4/1991 |
| JP | 05-76406 U | 10/1993 |
| JP | 2003-325497 A | 11/2003 |
| JP | 2005-131157 A | 5/2005 |
| JP | 2007-301284 A1 | 11/2007 |
| JP | 2009-298280 A | 12/2009 |
| JP | 2010-57546 A | 3/2010 |
| JP | 2012-29889 A | 2/2012 |
| JP | 2013-503778 A | 2/2013 |
| JP | 2013-146301 A | 8/2013 |
| JP | 2014-178308 A | 9/2014 |
| JP | 2014-195588 A | 10/2014 |

OTHER PUBLICATIONS

"Portable X-ray imaging apparatus IPF-21 Inverter type", Toshiba Medical Supply Co., Ltd., http://www.toshiba-irvouyouhin.co.ip/tmeds/xrays/ipf21_html (3 pages total) bearing 2004 copyright, downloaded from cache Dec. 19, 2017.

(56) References Cited

OTHER PUBLICATIONS

International Search Report for PCT/JP2016/002483 dated Sep. 27, 2016.
Notification of Reasons for Refusal drafted Sep. 7, 2016 issued by the Japanese Patent Office for corresponding Application No. 2015-141787.
Written Opinion dated Sep. 27, 2016 issued by the International Searching Authority in PCT/JP2016/002483.
International Preliminary Report on Patentability dated Jan. 16, 2018 issued by the International Bureau in PCT/JP2016/002483.
Communication dated Apr. 17, 2020, from the China National Intellectual Property Administration in application No. 201680040795.6.

* cited by examiner

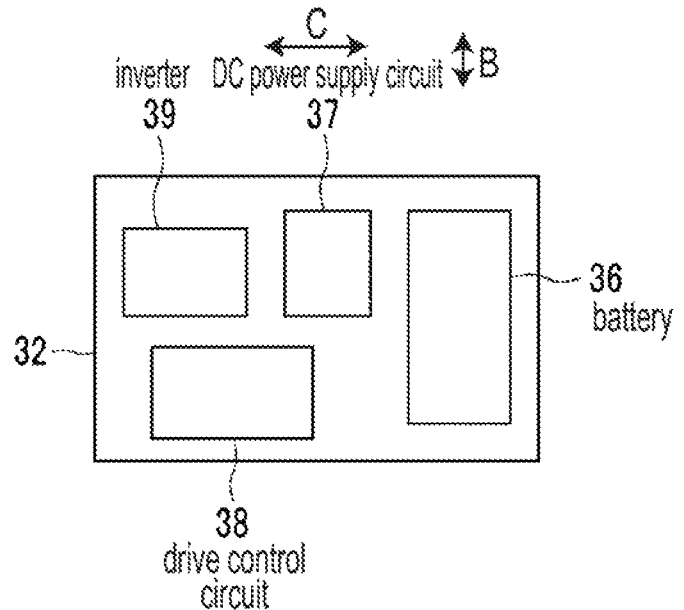
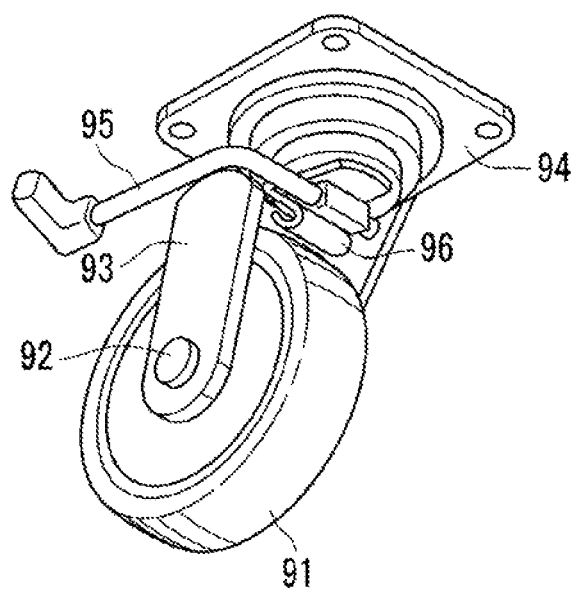

RADIOGRAPHIC IMAGING APPARATUS COMPRISING A LEG UNIT HAVING THREE OR MORE WHEEL UNITS

CROSS-REFERENCE TO RELATED APPLICATION

This application is a continuation application of International Application No. PCT/JP2016/002483, filed May 23, 2016, the disclosure of which is incorporated herein by reference in its entirety. Further, this application claims priority from Japanese Patent Application No. 2015-141787 filed Jul. 16, 2015, the disclosure of which is incorporated herein by reference in its entirety.

BACKGROUND OF THE INVENTION

1. Field of the Invention

The present invention relates to a radiographic imaging apparatus, and more particularly, to a radiographic imaging apparatus in which an arm unit or the like supports a radiation source.

2. Description of the Related Art

In the past, a portable radiation-irradiation device, on which only a minimum number of components for radiation irradiation, such as a radiation source and an electrical circuit, are mounted and which can be operated while being held by an operator, has been proposed as disclosed in, for example, JP2012-29889A and "Toshiba Medical Supply Co., Ltd., X-ray equipment IPF-21, [online], [Search on Jul. 30, 1999], Internet URL:http://www.toshiba-iryouyouhin.co.jp/tmeds/xrays/ipf21.html". Since this kind of portable radiation-irradiation device is reduced in weight so that an operator can hold and operate the radiation-irradiation device with hands, the radiation-irradiation device is advantageous for the imaging of a subject in various directions.

A cassette where a stimulable phosphor sheet (IP: Imaging Plate) or a silver halide film for an X-ray is received in a housing is generally used in a case in which the radiation image of a subject is to be taken using the above-mentioned portable radiation-irradiation device.

That is, in a case in which such a cassette is disposed at a position facing the radiation-irradiation device with a subject interposed therebetween and the radiation-irradiation device is driven in this state, the stimulable phosphor sheet or the like provided in the cassette is irradiated with radiation, such as X-rays, transmitted through the subject and the transmitted radiation image of the subject is recorded on the stimulable phosphor sheet or the like.

In recent years, there have also been many cases in which a so-called electronic cassette to be described later is used instead of the above-mentioned cassette. An example of this electronic cassette is disclosed in JP2014-178308A.

The portable radiation-irradiation device can be held and operated with hands by an operator. However, to prevent shaking and to prevent operator's hands or the like from being exposed to radiation, it is preferable that the portable radiation-irradiation device is used while being supported by a support device. "Toshiba Medical Supply Co., Ltd., X-ray equipment IPF-21, [online], [Search on Jul. 30, 1999], Internet URL:http://www.toshiba-iryouyouhin.co.jp/tmeds/xrays/ipf21.html" also discloses an example of such a support device, and particularly, a support device that includes wheel units provided at lower portions of legs and can travel.

A radiographic imaging apparatus having a structure in which the support device, which is adapted to be capable of traveling, and the portable radiation-irradiation device are combined with each other can easily image a subject in various directions and also has mobility. Accordingly, the radiographic imaging apparatus is suitable to be used in, for example, an emergency room or the like.

As disclosed in, for example, JP1993-76406U (JP-H05-76406U) and JP1991-99000A (JP-H03-99000A), a radiographic imaging apparatus of which a radiation source mounted on an arm unit is used is also publicly known. In many cases, this kind of radiographic imaging apparatus basically includes a leg unit, a body unit that receives a battery for driving a radiation source and an electrical circuit relating to the drive of the radiation source and is held on the leg unit, an arm unit that is connected to the body unit, and the radiation source that is mounted on the arm unit.

Since the radiographic imaging apparatus having the basic structure has advantages that the radiographic imaging apparatus can also be easily transported in a narrow place and can be used even in an environment where AC power cannot be used, the radiographic imaging apparatus is particularly suitably used to take the radiation image of a patient who is transferred to a medical facility, such as a hospital, or a patient who is lying on a bed in a small hospital room.

SUMMARY OF THE INVENTION

However, all of a radiographic imaging apparatus disclosed in "Toshiba Medical Supply Co., Ltd., X-ray equipment IPF-21, [online], [Search on Jul. 30, 1999], Internet URL:http://www.toshiba-iryouyouhin.co.jp/tmeds/xrays/ipf21.html", that is, the radiographic imaging apparatus in which the support device, which is adapted to be capable of traveling, and the portable radiation-irradiation device are combined with each other, and the radiographic imaging apparatuses disclosed in JP1993-76406U (JP-H05-76406U) and JP1991-99000A (JP-H03-99000A) are not moved in a small radius. Accordingly, there is room for improvement in the quick movement of the radiographic imaging apparatuses to a use position through a narrow place.

The invention has been made in consideration of the above-mentioned circumstances, and an object of the invention is to provide a radiographic imaging apparatus that can be quickly carried to a use position in a small radius.

A first radiographic imaging apparatus according to the invention comprises a leg unit that includes three or more wheel units and is capable of traveling on an apparatus-placement surface by using wheels, a body unit that is held on the leg unit, a radiation source support unit that is formed of an arm unit or the like connected to the body unit, a radiation source that is mounted on the radiation source support unit, a battery that is received in the body unit and drives the radiation source, and a circuit that is received in the body unit and relates to the drive of the radiation source. The wheel unit is composed of a revolving caster.

Further, the invention is to provide a second radiographic imaging apparatus in which an omnidirectionally moving wheel is applied instead of the revolving caster. That is, the second radiographic imaging apparatus comprises a leg unit that includes three or more wheel units and is capable of traveling on an apparatus-placement surface by using wheels, a body unit that is held on the leg unit, a radiation source support unit that is connected to the body unit, a radiation source that is mounted on the radiation source support unit, a battery that is received in the body unit and drives the radiation source, and a circuit that is received in the body unit and relates to the drive of the radiation source. The wheel unit is composed of an omnidirectionally moving wheel.

As in OMNI WHEEL (registered trademark) or a Mecanum wheel that are disclosed in, for example, JP2010-076630A, JP2012-030735A, and the like, the omnidirectionally moving wheel is formed of a rotating body that rotates about a rotation axis, which is horizontal during travel, and a plurality of rollers that are mounted on the rotating body along one circle coaxial with the rotating body. The omnidirectionally moving wheel can be moved in a first direction by the rotation of the rotating body, and can be moved in a second direction crossing the first direction by the rotation of the rollers. Here, the "horizontal" generally means that an element is parallel to the apparatus-placement surface in a state in which the leg unit is placed on the horizontal apparatus-placement surface. Further, the rotation axis of the roller is set to extend in a tangential direction of one circle coaxial with the rotating body or a direction close to the tangential direction.

In the radiographic imaging apparatus of the invention having the above-mentioned structure, as a particularly preferable aspect, the body unit is adapted to be rotatable relative to the leg unit about a rotation axis extending in a vertical direction, the radiation source support unit formed of an arm unit or the like protrudes from the body unit in one horizontal direction, and the body unit is formed in a shape where a length of the body unit in a direction parallel to the horizontal direction is shorter than a length of the body unit in a direction perpendicular to the horizontal direction in a plan view state.

Here, the "horizontal" generally means that an element is parallel to the apparatus-placement surface in a state in which the leg unit is placed on the horizontal apparatus-placement surface as described above. Further, a case in which an element protrudes from in the horizontal direction also includes a case in which an element obliquely protrudes while having a horizontal component. Furthermore, the "plan view state" means a state in which an element is projected onto the apparatus-placement surface.

Moreover, the "length" means the maximum length, and also means the maximum length in the horizontal direction likewise even in a case in which sides of the body unit are inclined with respect to the respective directions.

Further, it is preferable that, in a case in which the radiographic imaging apparatus of the invention is formed in the above-mentioned particularly preferable aspect, the body unit is formed in a shape where the length of the body unit in the direction parallel to the horizontal direction is equal to or shorter than ⅓ of the length of the body unit in the direction perpendicular to the horizontal direction in a plan view state.

Furthermore, it is preferable that, in a case in which the radiographic imaging apparatus of the invention is formed in the above-mentioned particularly preferable aspect, the body unit is inclined to a state in which an upper end of the body unit is closer to the radiation source than a lower end of the body unit.

Moreover, it is preferable that, in a case in which the radiographic imaging apparatus of the invention is formed in the above-mentioned particularly preferable aspect, the body unit has a structure where the battery and the circuit relating to the drive of the radiation source are received in a housing formed in the shape of a substantially rectangular parallelepiped.

Further, it is preferable that, in a case in which the radiographic imaging apparatus of the invention is formed in the above-mentioned particularly preferable aspect, the circuit relating to the drive of the radiation source is divided into a plurality of blocks and all the plurality of blocks are arranged in a direction crossing the horizontal direction.

Furthermore, in the radiographic imaging apparatus of the invention, it is preferable that, in a case in which a circular locus, which is drawn by the outermost end of the leg unit in a case in which the leg unit revolves on the apparatus-placement surface so that at least two wheel units follow a common circle, and the body unit are superimposed in a plan view state, the entire body unit is positioned inside the circular locus.

Here, the "outermost end" of the leg unit is the outermost end in the radial direction of the circular locus, that is, an end portion that is positioned so as to be most distant from the center of the circular locus in the radial direction. Further, the "outermost end" is not limited to the outermost end of the wheel unit. In a case in which a quadrangular base, which the wheel unit is mounted on the lower surface thereof and is wider than the wheel unit to the outside, or the like is provided, the "outermost end" may be the outermost end of the base or the like.

Furthermore, in the radiographic imaging apparatus of the invention, it is preferable that the radiation source support unit is adapted to be extendable and retractable.

Moreover, in the radiographic imaging apparatus of the invention, it is preferable that the radiation source is adapted to be rotatable about an axis parallel to a longitudinal direction of a portion of the radiation source support unit on which the radiation source is mounted.

Further, it is preferable that the radiographic imaging apparatus of the invention further includes oscillating-position fixing unit that fixes an oscillating position of the radiation source after the radiation source is adapted to be capable of oscillating in a direction where an elevation angle of a radiation-emission axis is changed. Furthermore, according to a case in which the radiographic imaging apparatus has the above-mentioned structure, particularly, it is preferable that, in a case in which the fixing of the oscillating position of the radiation source performed by the oscillating-position fixing unit is released, the radiation source is adapted to take an oscillating position at which the radiation-emission axis is lowered by the action of its own weight of the radiation source in comparison with a case in which the oscillating position of the radiation source is fixed.

Moreover, in the radiographic imaging apparatus of the invention, it is preferable that the wheel unit includes brake unit.

Further, it is preferable that the radiographic imaging apparatus of the invention further includes a height adjustment mechanism which is capable of adjusting a height to the radiation source support unit from the wheel unit.

Specifically, it is preferable that the above-mentioned height adjustment mechanism is composed of the leg unit of which an angle with respect to the horizontal direction is adjustable.

Alternatively, the height adjustment mechanism may be composed of a telescopic tube mechanism that is provided in at least a part of a gap between the wheel unit and the radiation source support unit.

In addition, the height adjustment mechanism may be composed of a lifting mechanism that raises and lowers a portion of the body unit connected to the radiation source support unit.

Since the wheel unit is composed of a revolving caster or an omnidirectionally moving wheel, the radiographic imaging apparatus of the invention can be moved in a front-back direction and a lateral direction, can also be moved along a large curve, and can revolve in place (that is, a human rotates about the axis of the body in the case of the human). Accordingly, the radiographic imaging apparatus of the invention can be quickly carried to a use position in a small radius.

BRIEF DESCRIPTION OF THE DRAWINGS

FIG. 9 is a schematic diagram showing another example of the state in which the plurality of circuits are disposed in the body unit.

FIG. 10 is a perspective view showing another example of the wheel unit that can be applied to the radiographic imaging apparatus of the invention.

DESCRIPTION OF THE PREFERRED EMBODIMENTS

Figure 1:
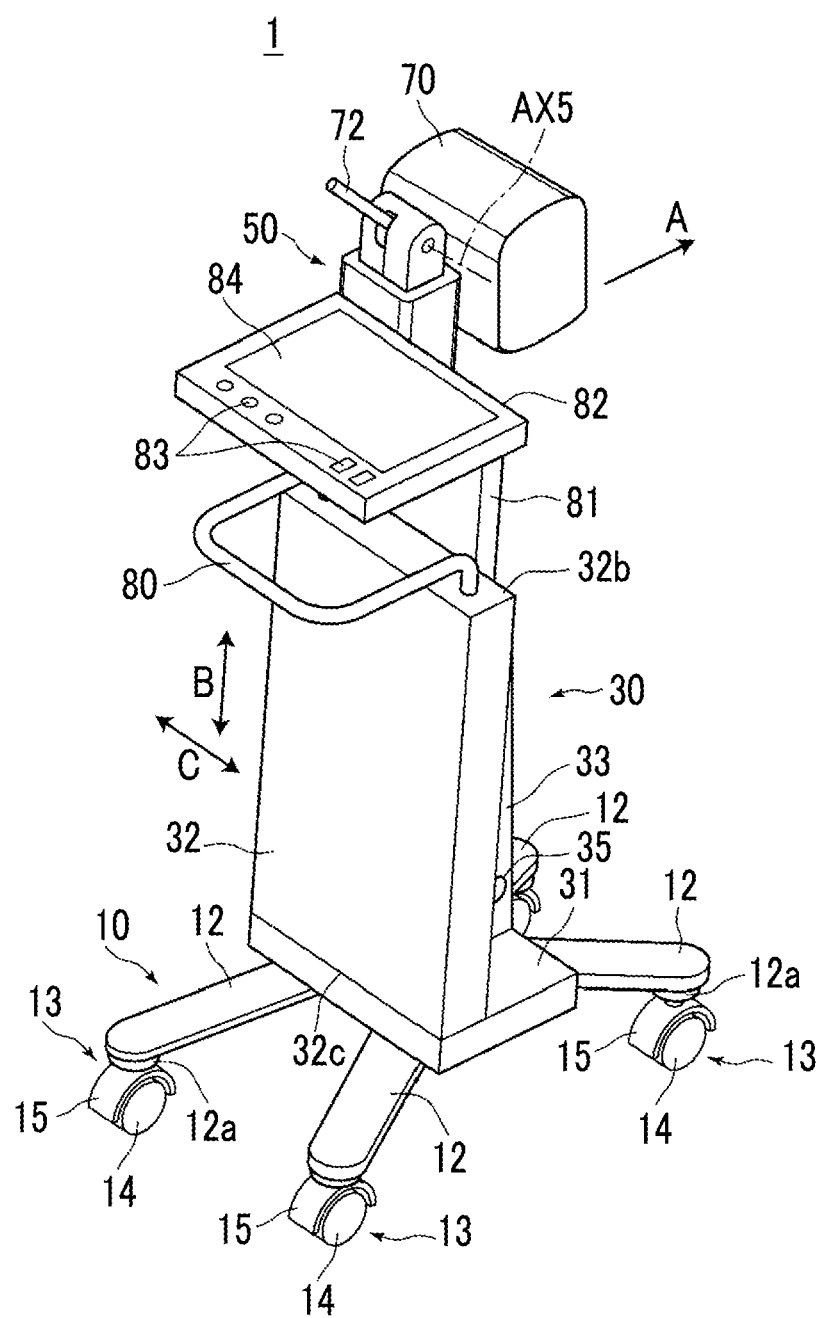
FIG. 1 is a perspective view of a radiographic imaging apparatus according to an embodiment of the invention.
Figure 2:
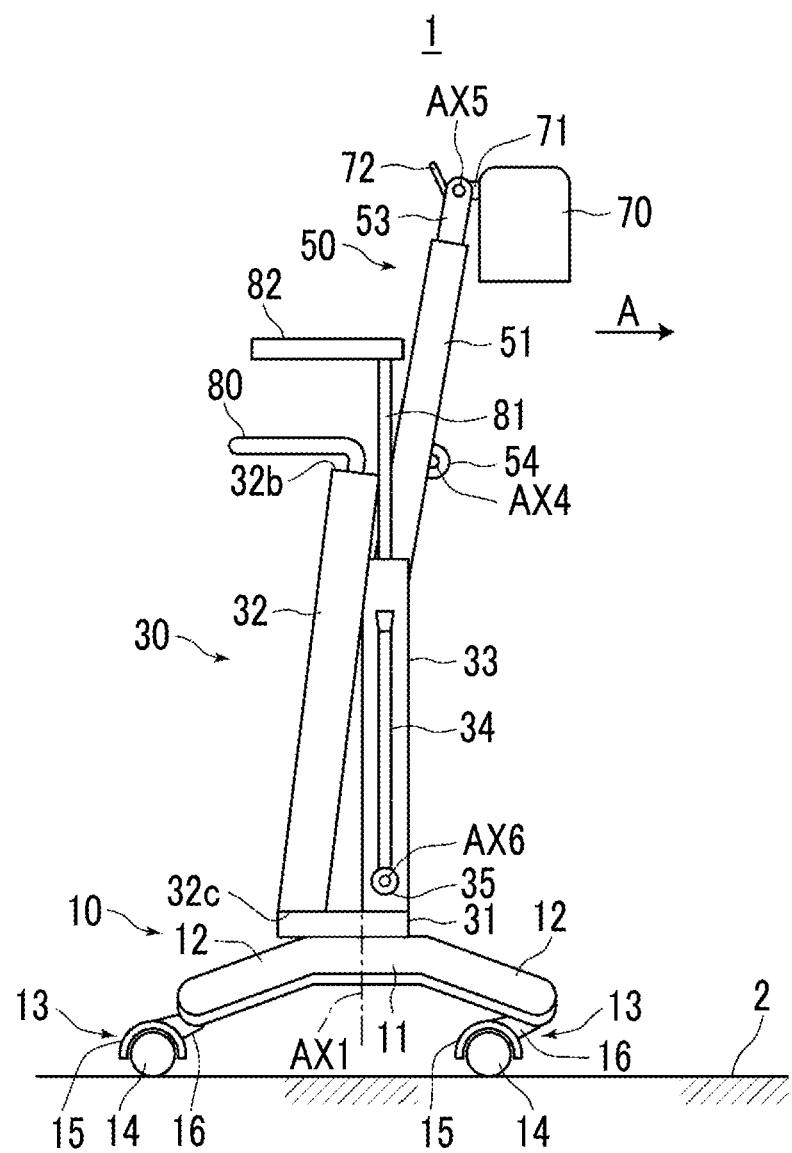
FIG. 2 is a side view showing a state in which the radiographic imaging apparatus of FIG. 1 is not in use.
Figure 3:
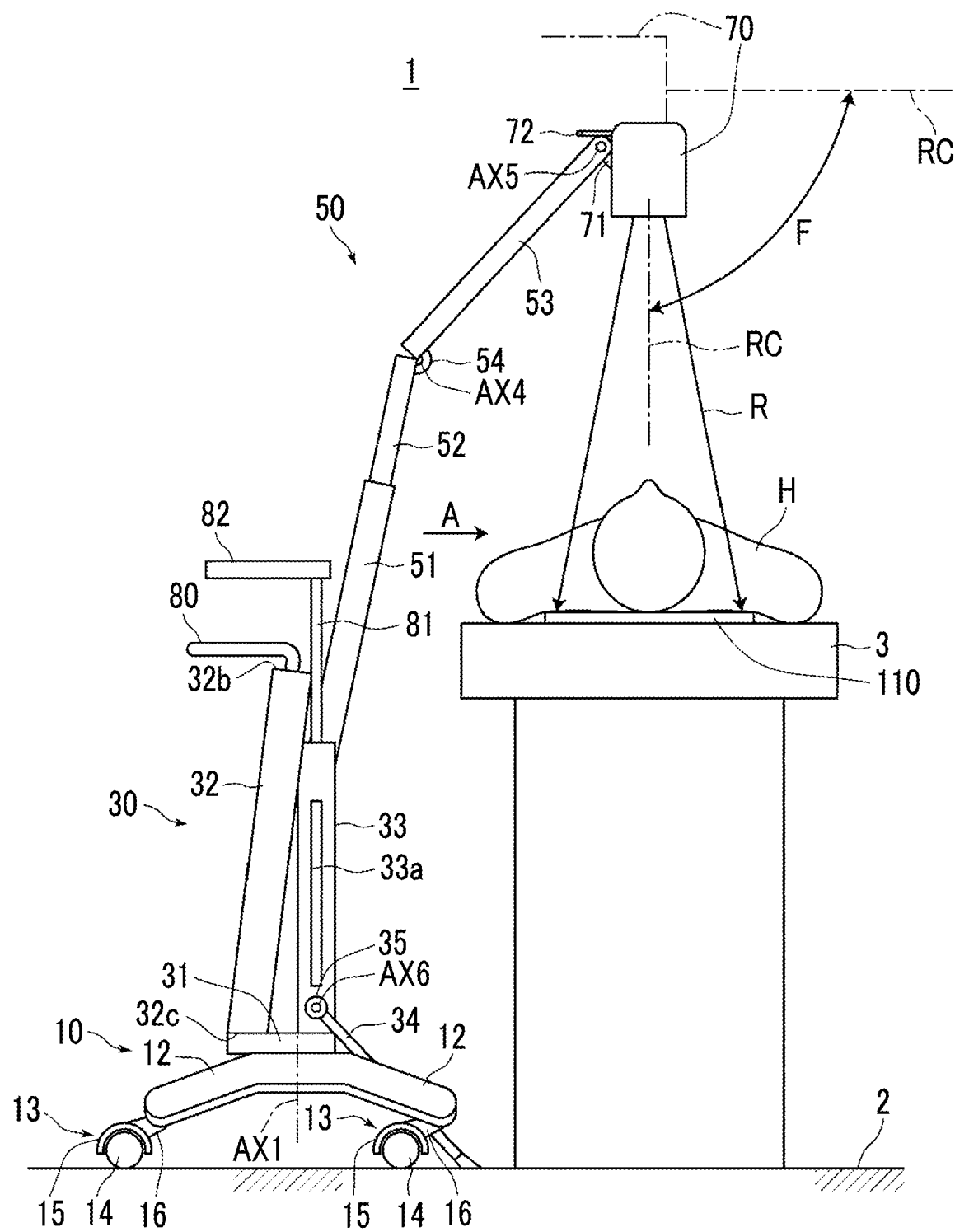
FIG. 3 is a side view showing a state in which the radiographic imaging apparatus of FIG. 1 is in use.
Figure 4:
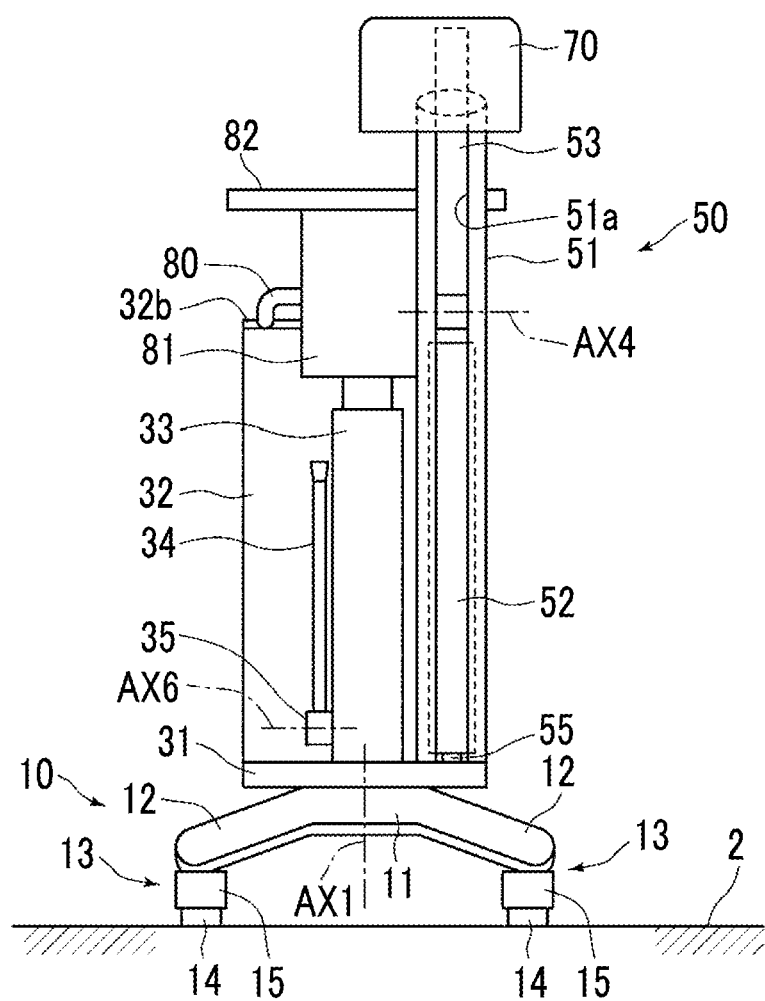
FIG. 4 is a rear view showing a state in which the radiographic imaging apparatus of FIG. 1 is not in use.
Figure 5:
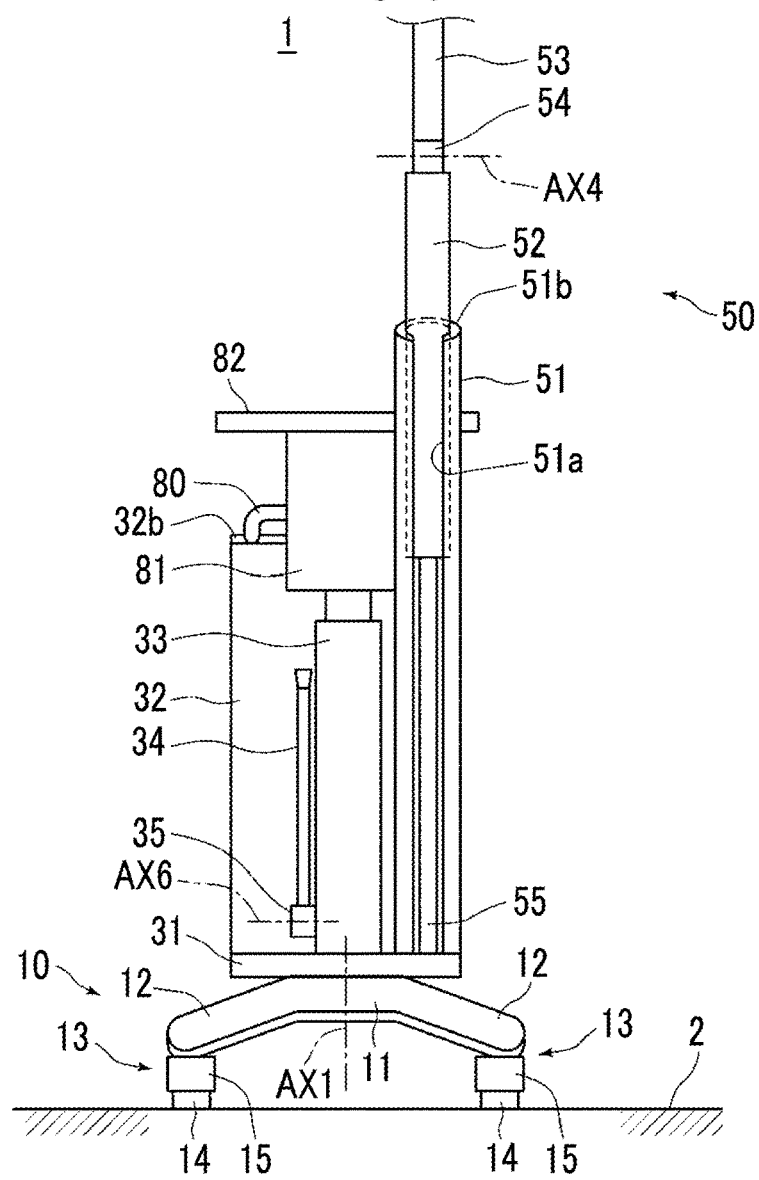
FIG. 5 is a rear view showing a state in which the radiographic imaging apparatus of FIG. 1 is in use.

A radiographic imaging apparatus according to an embodiment of the invention will be described in detail below with reference to the drawings. FIG. 1 is a perspective view showing the shape of the entire radiographic imaging apparatus 1 according to the embodiment of the invention, FIG. 2 is a side view showing a state in which the radiographic imaging apparatus 1 is not in use, FIG. 3 is a side view showing a state in which the radiographic imaging apparatus 1 is in use, FIG. 4 is a rear view showing a state in which the radiographic imaging apparatus 1 is not in use, and FIG. 5 is a rear view showing a state in which the radiographic imaging apparatus 1 is in use.

In the following description, the upper side and the lower side in a vertical direction in a state in which the radiographic imaging apparatus 1 is placed on an apparatus-placement surface 2, such as the floor, of a medical facility are referred to as "upper" and "lower", and a direction perpendicular to the vertical direction in the same state as the state is referred to as a "horizontal" direction.

As shown in FIGS. 1 to 5, the radiographic imaging apparatus 1 of this embodiment includes a leg unit 10 that can travel on an apparatus-placement surface 2, a body unit 30 that is held on the leg unit 10, an arm unit 50 as a radiation source support unit that is connected to the body unit 30, and a radiation source 70 that is mounted on a distal end portion of the arm unit 50. The body unit 30 and the arm unit 50 may be directly connected to each other, or may be indirectly connected to each other through some members.

The body unit 30 has a structure where an element, such as a battery to be described later, is received in a housing 32 fixed onto a base part 31 substantially having the shape of a thick plate. A handle 80, which is used to push or pull the radiographic imaging apparatus 1, is mounted on an upper end of the housing 32. Further, a holding member 33 is fixed onto the base part 31, and a console 82 is held at an upper portion of the holding member 33 through a pedestal 81.

The console 82 includes: input unit 83, such as operation buttons and switches, which are used to input signals and the like for instructing the radiographic imaging apparatus 1 to perform various operations; display unit 84 that is used to display the state of the radiographic imaging apparatus 1, information input by the input unit 83, and the like; and the like. The display unit 84 is formed of a so-called touch panel, and signals and the like may be input by a contact operation on the touch panel and the input unit 83 may be omitted.

The leg unit 10 includes a horizontal base 11, four legs 12 that extend outward from corner portions of the horizontal base 11 by way of example, and wheel units 13 that are mounted on wheel mounting portions 12a provided on lower surfaces of distal end portions of the respective legs 12. The above-mentioned base part 31 is held on the horizontal base 11 so as to be rotatable about a rotation axis AX1 extending in the vertical direction. Accordingly, the body unit 30 fixed to the base part 31 and the arm unit 50 to be described later are adapted to be rotatable relative to the leg unit 10 about the rotation axis AX1, that is, in a horizontal plane.

Figure 6:
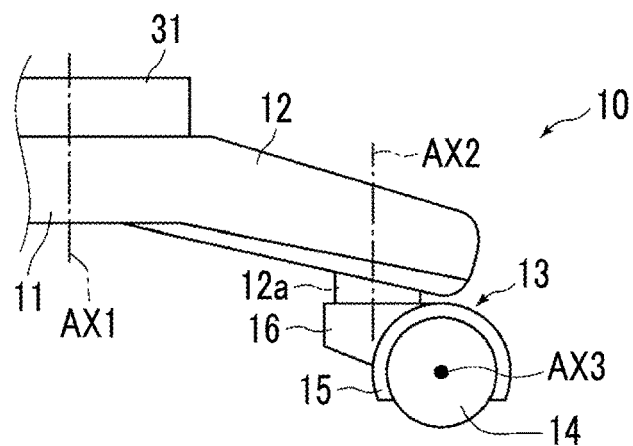
FIG. 6 is a side view of a wheel unit of the radiographic imaging apparatus of FIG. 1.

FIG. 6 is a view showing the side shape of a portion near the wheel unit 13. As shown in FIG. 6, the wheel unit 13 is formed of a so-called revolving caster that can revolve about a revolution axis AX2 extending in the vertical direction. That is, the wheel unit 13 includes a wheel 14 that is formed of, for example, a rubber tire or the like, a wheel holder 15 that holds the wheel 14 to allow the wheel 14 to be rotatable about a horizontal axle AX3, and a revolving part 16 that is integrated with the wheel holder 15; and the revolving part 16 is mounted on the wheel mounting portion 12a of the leg 12 so as to be revolvable about the revolution axis AX2.

The revolution axis AX2 is set to a position that is offset from the axle AX3 in the horizontal plane. Accordingly, in a case in which the leg unit 10 is moved in one horizontal direction, the revolving part 16 revolves so that the revolution axis AX2 is positioned on the front side in this direction and the wheel 14 is positioned on the rear side and the wheel 14 can be freely rotated. Accordingly, in a case in which a worker, such as a radiographer, grips the above-mentioned handle 80 and pushes or pulls the radiographic imaging apparatus 1, the worker can simply and quickly move the radiographic imaging apparatus 1 in an arbitrary direction.

Further, the four wheel units 13 are disposed in this embodiment so that each revolution axis AX2 is positioned at one corner of a common rectangle in a plan view state, that is, a state in which the wheel units 13 are projected onto the apparatus-placement surface 2. Accordingly, the entire leg unit 10 can also be rotated about a vertical line substantially passing through the position of the centroid of the rectangle in the horizontal plane, that is, on the apparatus-placement surface 2. In a case in which the leg unit 10 is rotated as described above, the four wheel units 13 travel while drawing a circular arc so as to follow a common circle.

Casters widely used in, for example, an office chair with casters, a wagon with casters for article transport, a work table with casters, or the like having been publicly known in the past can be appropriately selected and applied as the above-mentioned revolving caster forming the wheel unit 13.

Figure 11:
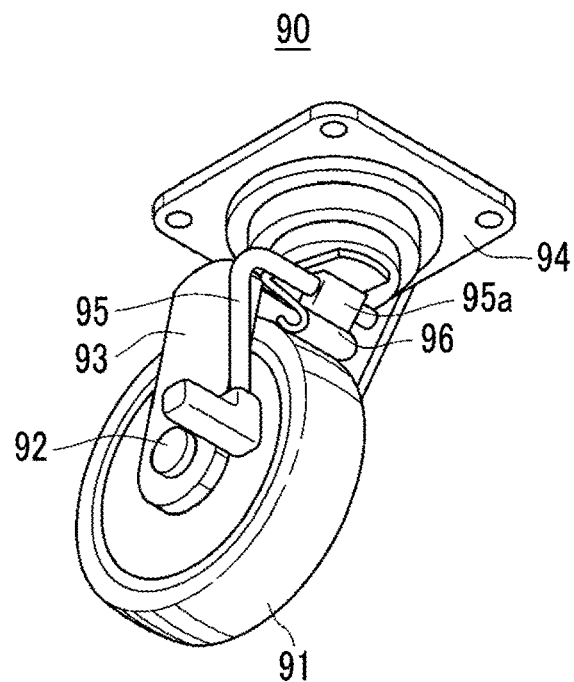
FIG. 11 is a perspective view showing that the wheel unit of FIG. 10 is in another state.

A wheel unit including brake unit may be used instead of the above-mentioned wheel unit 13. FIGS. 10 and 11 are perspective views showing an example of a wheel unit 90 including brake unit, FIG. 10 shows the state of the wheel unit 90 in a case in which a brake is released, and FIG. 11 shows the state of the wheel unit 90 in a case in which a brake is operated.

As shown in FIGS. 10 and 11, the wheel unit 90 includes a wheel 91 that is formed of, for example, a rubber tire or the like, a wheel holder 93 that holds the wheel 91 to allow the wheel 91 to be rotatable about an axle 92, a mounting seat 94 that holds the wheel holder 93 to allow the wheel holder 93 to be revolvable, a crank-shaped brake lever 95 that is held by the wheel holder 93, and a leaf spring 96. The brake lever 95 is held by the wheel holder 93 so as to be rotatable about a shaft thereof close to a proximal end (close to a right end in FIGS. 10 and 11).

In a case in which the brake lever 95 is at a rotational position of FIG. 10, the leaf spring 96 is separated from the wheel 91. Accordingly, the wheel 91 is rotatable. In a case in which the brake lever 95 is rotated from this state and is moved to a rotational position of FIG. 11, a protruding portion 95a formed on the shaft of the brake lever 95 close to the proximal end pushes the leaf spring 96 so that the leaf spring 96 is in pressure contact with the peripheral surface of the wheel 91. Accordingly, the wheel 91 cannot be rotated and the wheel 91 is in a braking state.

In a case in which the wheel units 90 including the above-mentioned brake unit are applied to the leg unit 10 and the wheels 91 are braked after the leg unit 10 is made to travel to move the radiographic imaging apparatus 1 to a predetermined position, the careless movement of the radiographic imaging apparatus 1 can be prevented.

Further, a revolving caster that includes brake unit that prevents a revolving part from revolving about a revolution axis (AX2 in the case of an example of FIG. 6) is also provided as the revolving caster. In a case in which such a revolving caster is applied, the careless movement of the radiographic imaging apparatus 1 caused by the revolution of each revolving part can be prevented while the rotation of each wheel is allowed. The wheel unit including that kind of brake unit can also be applied to the invention, and a wheel unit, which can brake both the rotation of the wheel and the revolution of the revolving part, can also be applied to the invention.

Furthermore, for example, a button or a lever, which is installed near the handle 80, other than the above-mentioned brake lever 95 may be operated to brake the wheel unit 13. Further, the wheel unit 13 may be adapted to be automatically braked in a case in which the moving speed of the wheel unit 13 is detected and the detected moving speed exceeds a certain set speed. Furthermore, in a case in which the detected moving speed exceeds the certain set speed, an alert using warning sound, the flicker of a lamp, or the like may be generated to alert a user of the apparatus. Only such an alert may be generated, and the wheel unit 13 may be braked together with the generation of the alert.

In addition, the wheel unit 13 may be adapted to be automatically braked in a case in which the separation of the hands of a user of the apparatus from the handle 80 is detected. Further, to prevent the fall of the radiographic imaging apparatus 1 in a case in which the wheel unit 13 is automatically braked as described above, it is preferable that the wheel unit 13 is adapted to be completely braked after the speed of the wheel unit 13 is gradually reduced. Further, in a case in which the wheel unit 13 is automatically braked, it is preferable that the four wheel units 13 are simultaneously braked.

Furthermore, the radiographic imaging apparatus 1 may be adapted to automatically brake and lock the wheel units 13 so as to eventually prevent the radiation source 70 from moving in a case in which a radiation image is taken. In this case, it is preferable that the radiographic imaging apparatus 1 is adapted to detect a certain operation immediately before the drive of the radiation source 70 and to automatically brake the wheel units 13 in a case in which the certain operation is detected. Examples of the above-mentioned operation include a release operation of a camera that takes an optical image used to check a radiation-irradiation range.

Figure 7:
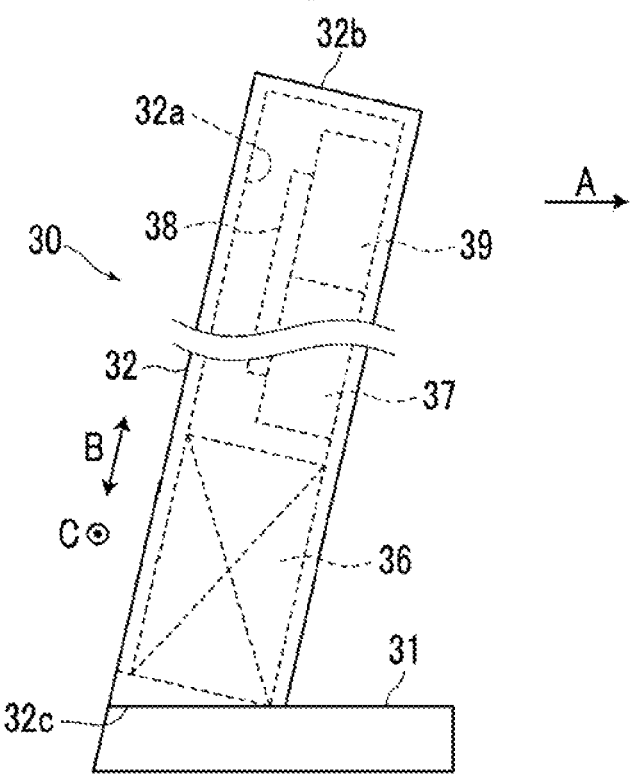
FIG. 7 is a side view of a body unit, which is partially broken, of the radiographic imaging apparatus of FIG. 1.
Figure 8:
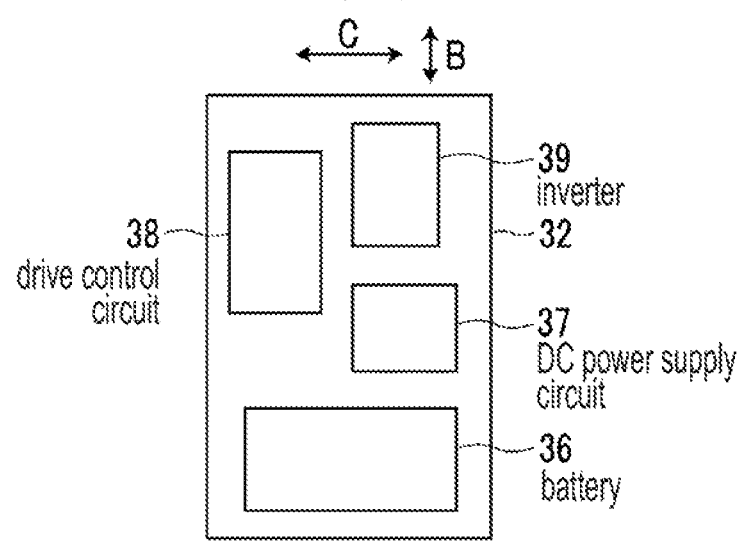
FIG. 8 is a schematic diagram showing a state in which a plurality of circuits are disposed in the body unit of FIG. 7.

Next, the body unit 30 will be described in detail with reference to FIGS. 7 and 8. FIG. 7 is a side view of the body unit 30 that is partially broken. As clearly shown in FIGS. 1 and 7, the housing 32 of the body unit 30 is formed substantially in the shape of a thin rectangular parallelepiped, and an opening (not shown) is provided on the front surface of the housing 32, that is, the surface of the housing 32 from which the handle 80 protrudes, and the opening is closed by a lid 32a.

In this embodiment, the housing 32 of the body unit 30 is fixed to the base part 31 in a state in which the housing 32 is inclined so that an upper end 32b is closer to the radiation source 70 than a lower end 32c. Arrow A shown in FIG. 7 corresponds to arrow A of FIG. 1, and the radiation source 70 is positioned on the front side of the housing 32 in the direction of arrow A in FIG. 7. The housing 32 may be formed separately from the base part 31 and may then be fixed to the base part 31, or may also be formed integrally with the base part 31 from the beginning.

A DC power supply circuit 37, a drive control circuit 38, and an inverter (DC-AC conversion circuit) 39 are received in the housing 32 in addition to a battery 36 for driving the radiation source 70. These circuits 37 to 39, which are divided into blocks, are publicly known circuits that relate to the drive of the radiation source 70, and examples of these are disclosed in JP2000-127834A. The replacement, maintenance and inspection, repair, and the like of the battery 36 and the circuits 37 to 39 can be performed through the opening in a state in which the lid 32a is opened.

As clearly shown in FIGS. 2 and 3, the arm unit 50 protrudes from the body unit 30 in one horizontal direction (the direction of arrow A), but all the circuits 37 to 39, which are divided into blocks, are arranged in directions crossing the direction of arrow A. In more detail, as in the schematic arrangement state shown in FIG. 8, the circuits 37 to 39 are arranged in the direction of arrow B crossing the direction of arrow A and in the direction of arrow C crossing the direction of arrow A. The direction of arrow B and the direction of arrow C are the longitudinal direction and the lateral direction of the housing 32 formed substantially in the shape of a thin rectangular parallelepiped. Since the circuits 37 to 39 are arranged in these directions, the housing 32, that is, the body unit 30 can be formed to be thinner. Further, since the battery 36 is also particularly arranged in the direction of arrow B together with the circuits 37 to 39 in this embodiment, this arrangement is more advantageous for the formation of the thin body unit 30.

In this embodiment, the housing 32 is formed in a shape where a length in the longitudinal direction is longer than a length in the lateral direction. However, as in the schematic shape shown in FIG. 9, the housing 32 may also be formed in a shape where a length in the longitudinal direction is shorter than a length in the lateral direction. Since the battery 36 and the circuits 37 to 39 are arranged in directions crossing the direction of arrow A even in this case, the body unit 30 can be formed to be thin. In a case in which the housing 32 is formed to be significantly long in the longitudinal direction or to be significantly long in the lateral direction, the battery 36 and the circuits 37 to 39 may be arranged only in the direction of arrow B or only in the direction of arrow C.

As clearly shown in FIGS. 2 and 3, a base portion 35 of a rod-like auxiliary leg 34 is mounted on the side surface of the holding member 33 so that the rod-like auxiliary leg 34 is rotatable about a rotation axis AX6. Further, as clearly shown in FIG. 3, the holding member 33 is provided with a slit 33a extending inward from the side surface of the holding member 33. For example, an electronic cassette or the like to be described later can be received in the slit 33a.

Here, a size relationship between the leg unit 10 and the body unit 30 will be described with reference to FIG. 12. As described above, the leg unit 10 is revolvable on the apparatus-placement surface 2 so that the four wheel units 13 follow a common circle. The radiographic imaging apparatus 1 is revolvable by the leg unit 10 to change the traveling direction thereof or to allow the radiation source 70 to face a desired direction, but the above-mentioned revolution is the revolution in the "smallest" radius. That is, the revolution of the leg unit 10, which revolves about a vertical line not present inside the four wheel units 13 in a plan view state so that the four wheel units 13 follow circles different from each other, is the revolution in a large radius. The above-mentioned revolution in the "smallest" radius correspond to a case in which the leg unit 10 revolves so that at least two wheel units 13 follow a common circle.

Figure 12:
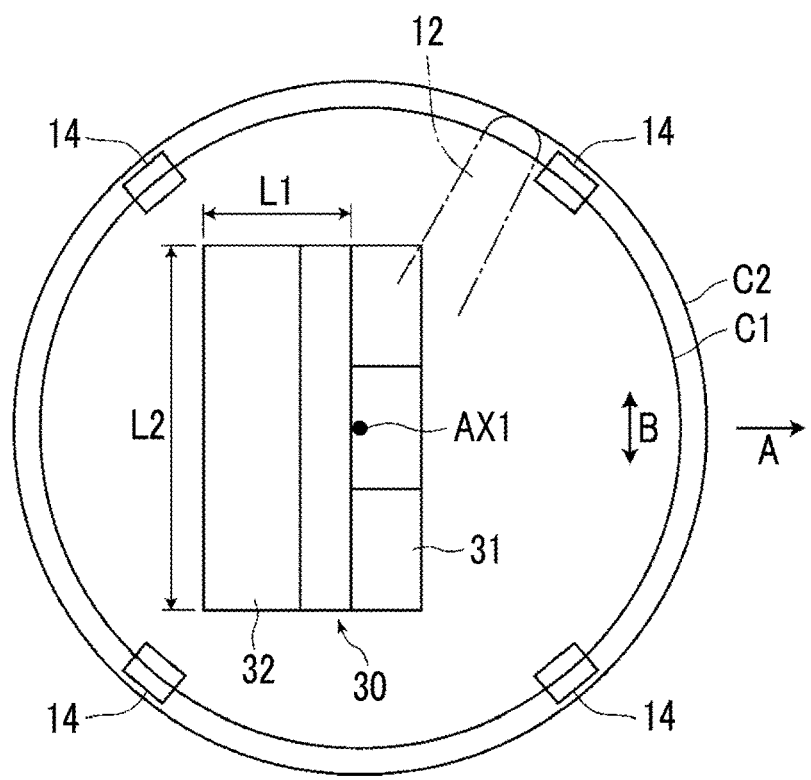
FIG. 12 is a diagram illustrating a size relationship between the body unit and a leg unit of the radiographic imaging apparatus of FIG. 1.

In FIG. 12, a common circle where the four wheel units 13 follow in a case in which the leg unit 10 revolves in the smallest radius is denoted by C1 and a circular locus drawn by the outermost end of the leg 12 (that is, the outermost end of the leg unit 10) in this case is denoted by C2. Further, FIG. 12 shows a state in which the body unit 30 and the base part 31 provided on the leg unit 10 are shown in plan view. As shown in FIG. 12, the body unit 30 is present inside the circular locus C2 drawn by the outermost end of the leg unit 10. Likewise, the base part 31 is also present inside the circular locus C2.

According to the above-mentioned structure, if the user of the apparatus pays attention so that the outermost end of the leg 12 does not bump against anything in a case in which the user of the apparatus revolves the radiographic imaging apparatus 1 in the smallest radius to change the direction of the radiation source 70, the user of the apparatus can avoid the bump of the body unit 30 or the base part 31 against something.

Further, as shown in FIG. 12, the body unit 30 is formed in a shape where the length L1 of the body unit 30 in a direction (the direction of arrow A) in which the arm unit 50 protrudes from the body unit 30 is shorter than the length L2 of the body unit 30 in a direction (the direction of arrow B) perpendicular to the direction in a state in which the body unit 30 is shown in plan view. Since the body unit 30 is formed such a shape, the radiographic imaging apparatus 1 can be formed in a slim shape that does not occupy a wide place in a case in which the arm unit 50 is most reduced in length and is received in a tubular member 51 as described later. It is preferable that the length L1 is generally shorter than ⅓ of the length of the length L2.

The body unit 30 has been adapted to be rotatable relative to the leg unit 10 about the rotation axis AX1 as described above, but it is preferable that the body unit 30 is provided with lock unit that prevents the rotation of the body unit 30. A component having a structure, which simultaneously locks the rotation of the body unit 30 in a case in which the component brakes the wheel unit 13 while interlocking with brake operating unit (for example, the brake lever 95 of FIG. 10, or the like) that brakes the wheel unit 13, is preferable as the lock unit. Alternatively, a component having a structure, which locks the rotation of the body unit 30 by an independent operation, may be used as the lock unit. If that kind of lock unit is provided, the rotation of the body unit 30 caused at the time of rotation of the radiation source 70 can be prevented in a case in which the radiation source 70 is adapted to be rotatable relative to the arm unit 50 about a rotation axis AX9 (see FIG. 16) as described later.

Returning to FIGS. 1 to 5, the arm unit 50 will be described in detail below. The arm unit 50 includes a tubular member 51 that has a substantially "C"-shaped cross-sectional shape formed by a slit 51a extending in an axial direction and provided at a part of a substantially cylindrical member, a body-side arm 52 (a body-side part of the arm unit) that can be received in the tubular member 51 so as to be movable in the axial direction, and a radiation source-side arm (a radiation source-side part of the arm unit) 53 that can be received in the tubular member 51 so as to be movable in the axial direction likewise. The tubular member 51 is fixed onto the base part 31 in a state in which the tubular member 51 is inclined in substantially the same direction as the housing 32 inclined as described above. The tubular member 51 may be formed of a cylindrical member or a rectangular cylindrical member other than the member having a substantially "C"-shaped cross-sectional shape as described above, and may be formed of half-split members having a cross-sectional shape in which two circular arcs face each other.

A lower end portion of the radiation source-side arm 53 is connected to an upper end portion of the body-side arm 52 through a revolution-holding mechanism 54 so as to be revolvable about a revolution axis AX4. The revolution axis AX4 is an axis extending in the horizontal direction. The radiation source-side arm 53 revolves about the revolution axis AX4 in a direction where an angle between the radiation source-side arm 53 and the body-side arm 52 changes. The revolution-holding mechanism 54 holds both the radiation source-side arm 53 and the body-side arm 52 so that the radiation source-side arm 53 revolves with respect to the body-side arm 52 through a friction mechanism. Accordingly, the radiation source-side arm 53 can revolve in a case in which an external force, which is strong to some extent, is applied to the radiation source-side arm 53, and the radiation source-side arm 53 maintains an angle relative to the body-side arm 52 without revolving as long as an external force is not applied.

The body-side arm 52 includes a cylinder (not shown) forming a gas spring built therein, and forms the body-side part of the arm unit together with a piston rod 55 combined with the cylinder. The gas spring basically includes the cylinder that is filled with gas, a piston that partitions the inside of the cylinder into an upper chamber and a lower chamber, a communication passage that allows these upper and lower chambers to communicate with each other, an on-off valve that opens and closes the communication passage, an operation lever that operates the on-off valve, and the piston rod 55 of which an upper end is connected to the piston.

In the past, the gas spring having the above-mentioned structure has been widely applied as a height adjustment mechanism in a chair of which the height of a seating surface can be changed, or the like. In this embodiment, the body-side part (formed of the body-side arm 52 and the piston rod 55) of the arm unit are adapted to be capable of extending and retracting so that the length of the arm unit 50 can be adjusted. This will be described in detail below.

In a case in which, for example, the operation lever is pulled to keep the on-off valve in an open state, the upper and lower chambers communicate with each other and gas can flow between the upper and lower chambers. Accordingly, the cylinder, that is, the body-side arm 52 is movable relative to the piston rod 55. Therefore, in a case in which a force, which is large to some extent, is applied to push the body-side arm 52 down in the tubular member 51, the entire body-side arm 52 is received in the tubular member 51 as shown in FIG. 4. In this case, a part of the radiation source-side arm 53 is also received in the tubular member 51 in a state in which the longitudinal direction of the radiation source-side arm 53 is aligned with the longitudinal direction of the body-side arm 52. In a case in which the body-side arm 52 and the radiation source-side arm 53 are received in the tubular member 51 in this way, the revolution-holding mechanism 54 is moved in the slit 51a of the tubular member 51.

In a case in which the radiographic imaging apparatus 1 is not in use, the arm unit 50 is in a state shown in FIG. 4. Since a part of the radiation source-side arm 53 is positioned in the tubular member 51 in this state, the radiation source-side arm 53 cannot revolve about the revolution axis AX4. That is, in this embodiment, the tubular member 51 functions as revolution regulating unit that allows the radiation source-side arm 53 not to revolve in a state in which the body-side part of the arm unit 50 is shorter than a predetermined length. The "predetermined length" in this case is the length of the body-side part of the arm unit 50 (the total length of the body-side arm 52 and a portion of the piston rod 55 protruding from the body-side arm 52) that allows the lower end of the radiation source-side arm 53 to slightly get out of the tubular member 51.

In a case in which the operation lever is released after the arm unit 50 is in the state shown in FIG. 4, the on-off valve is in a closed state and the flow of gas is regulated. Accordingly, the state of the arm unit 50 is kept. After that, in a case in which the operation lever is operated so that the on-off valve is in the open state, the body-side arm 52 is movable relative to the piston rod 55 as described above and the body-side arm 52 is moved up in the tubular member 51 by the repulsive force of gas compressed in the upper chamber. In this case, the body-side arm 52 can be moved up to a position at which the upper end of the body-side arm 52 protrudes from the tubular member 51 as shown in FIG. 3. Since the entire radiation source-side arm 53 also gets out of the tubular member 51 in this state, the radiation source-side arm 53 is revolvable about the revolution axis AX4.

If the operation lever is released and the on-off valve in the closed state in a case in which the on-off valve is in the open state as described above and the body-side arm 52 is moved up in the tubular member 51, the flow of gas is regulated and the body-side arm 52 is stopped at a position at that time. In this way, the length of a portion of the body-side arm 52, which protrudes from the tubular member 51, that is, the entire length of the arm unit 50 can be adjusted.

The radiation source 70 has a structure where, for example, an X-ray tube, a booster circuit, cooling unit that cools the X-ray tube, and the like are received in a housing. Further, the radiation source 70 is mounted on the distal end portion of the above-mentioned radiation source-side arm 53 through a support member 71 so as to be capable of oscillating about an oscillation axis AX5. The oscillation of the radiation source 70 is oscillation in a direction where an elevation angle of a radiation-emission axis RC is changed as shown in FIG. 3 by arrow F. Since the direction of the radiation-emission axis RC is changed in a case in which the radiation source 70 can oscillate in this way, the radiation images of subjects, which are in various positions, can be taken.

The oscillating position of the radiation source 70, which is adapted to be capable of oscillating, is adapted to be capable of being fixed by the operation of a lock lever 72. Further, in a case in which the fixing of the oscillating position performed by the lock lever 72 is released, the radiation source 70 is adapted to take an oscillating position at which the radiation-emission axis RC is lowered by the action of its own weight of the radiation source 70 in comparison with a case in which the oscillating position of the radiation source 70 is fixed. The oscillating position at which the radiation-emission axis RC is lowered is most preferably an oscillating position at which the radiation-emission axis RC is directed downward in the vertical direction. According to the above-mentioned structure, after the taking of the radiation image of, for example, a subject ends and the radiographic imaging apparatus 1 is moved in the lateral direction so as to be separated from the subject, it is possible to prevent the subject from being irradiated with radiation by mistake.

Next, the taking of a radiation image performed by the radiographic imaging apparatus 1 having the above-mentioned structure will be described. In the state which is shown in FIG. 2 and in which the radiographic imaging apparatus 1 is in not in use, the radiographic imaging apparatus 1 is transported to a use position while the radiographic imaging apparatus 1 is made to travel on the apparatus-placement surface 2, such as the floor, of a hospital by the wheel units 13 of the leg unit 10. In this case, since the wheel units 13 are composed of the above-mentioned revolving casters, the radiographic imaging apparatus 1 can be moved in a front-back direction and the lateral direction, and can also be moved along a large curve, and can also revolve at that position. Accordingly, the radiographic imaging apparatus 1 can be quickly transported to a use position in a state in which the radiographic imaging apparatus 1 revolves in a small radius.

The taking of a radiation image is performed on a subject H who is supine on a supine table 3, such as a bed, as shown in, for example, FIG. 3. In a case in which the radiographic imaging apparatus 1 is set at an imaging position shown in FIG. 3, the radiographic imaging apparatus 1 can also be moved in the height direction of a subject H, that is, in the form of so-called the side-crawl by the wheel units 13 formed of revolving casters. Accordingly, the radiographic imaging apparatus 1 can be easily set to the optimum position.

In this case, since the body unit 30 is formed in a thin shape as a whole as described above and the holding member 33 is also formed in a thin shape, the radiographic imaging apparatus 1 can also easily enter, for example, a narrow space between beds. Further, since the body unit 30 and the holding member 33 are formed in a thin shape as a whole, the radiographic imaging apparatus 1 can also be set to a position very close to the bed while the leg unit 10 is inserted into a space under the bed. Accordingly, since the adjustment of the position of the radiation source 70, which is caused by the extension, the retraction, and the revolution of the arm unit 50, may be less performed, time required to take an image can be shortened.

After the radiographic imaging apparatus 1 is set to the optimum position, the body-side arm 52 of the arm unit 50 extends to an arbitrary position where the body-side arm 52 protrudes from the tubular member 51 as described above. After that, the radiation source-side arm 53 of the arm unit 50 is made to revolve about the revolution axis AX4 so that the radiation source 70 is set to the optimum position, and the radiation source 70 is made to oscillate about the oscillation axis AX5 so that the radiation-emission axis RC is set to the optimum direction.

Furthermore, since the base part 31 holding the arm unit 50 is adapted to be rotatable on the leg unit 10 about the rotation axis AX1 in this embodiment, the direction of the arm unit 50 can also be changed by the rotation of the base part 31 to adjust the position and direction of the radiation source 70.

Since the radiation source-side arm 53 of the arm unit 50 cannot revolve due to the action of the tubular member 51 as described above in a case in which the body-side arm 52 does not extend to a position where the body-side arm 52 protrudes from the tubular member 51, it is possible to prevent a problem that the radiation source-side arm 53 revolves and the radiation source 70 bumps against a subject H in a state in which the radiation source 70 is at a relatively low position. Further, since the arm unit 50 protrudes in a direction (the direction of arrow A) where the arm unit 50 is closer to the subject H than the body unit 30, the radiation source 70 can be disposed so as to face the subject H who is present at a position distant from the body unit 30.

In this case, the rod-like auxiliary leg 34 is rotated about the rotation axis AX6 to be in a state in which the distal end of the rod-like auxiliary leg 34 is in contact with the apparatus-placement surface 2 as shown in FIG. 3. For example, a member hard to slip, such as rubber, is mounted on the distal end of the auxiliary leg 34 to prevent slip. The auxiliary leg 34 in this state functions as a so-called "tension rod", and prevents the radiographic imaging apparatus 1 from falling down toward the distal end of the radiation source-side arm 53 by which the heavy radiation source 70 is held. For example, a member having the shape of an outrigger for preventing the fall of a crane truck is received in the holding member 33 instead of the above-mentioned auxiliary leg 34, and may be pulled in the direction of arrow A and be used in a case in which a radiation image is to be taken.

For example, an electronic cassette 110 to be described later is disposed under the subject H and the electronic cassette 110 is irradiated with radiation (for example, X-rays) R emitted from the radiation source 70 through the subject H, so that the taking of a radiation image in this example is performed. A command, which drives the radiation source 70, or the like is made by the console 82. Further, a cassette where a stimulable phosphor sheet (IP: Imaging Plate) or a silver halide film for an X-ray publicly known in the related art is received in a housing may be used instead of the electronic cassette 110.

Figure 14:
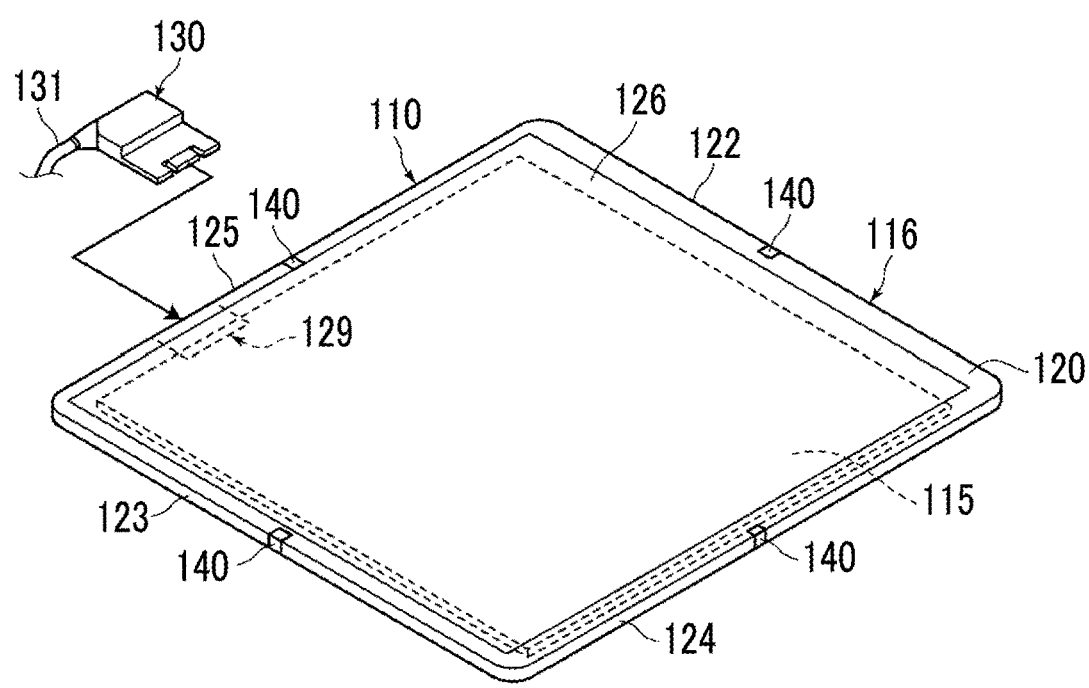
FIG. 14 is a perspective view showing the front side of an electronic cassette.
Figure 15:
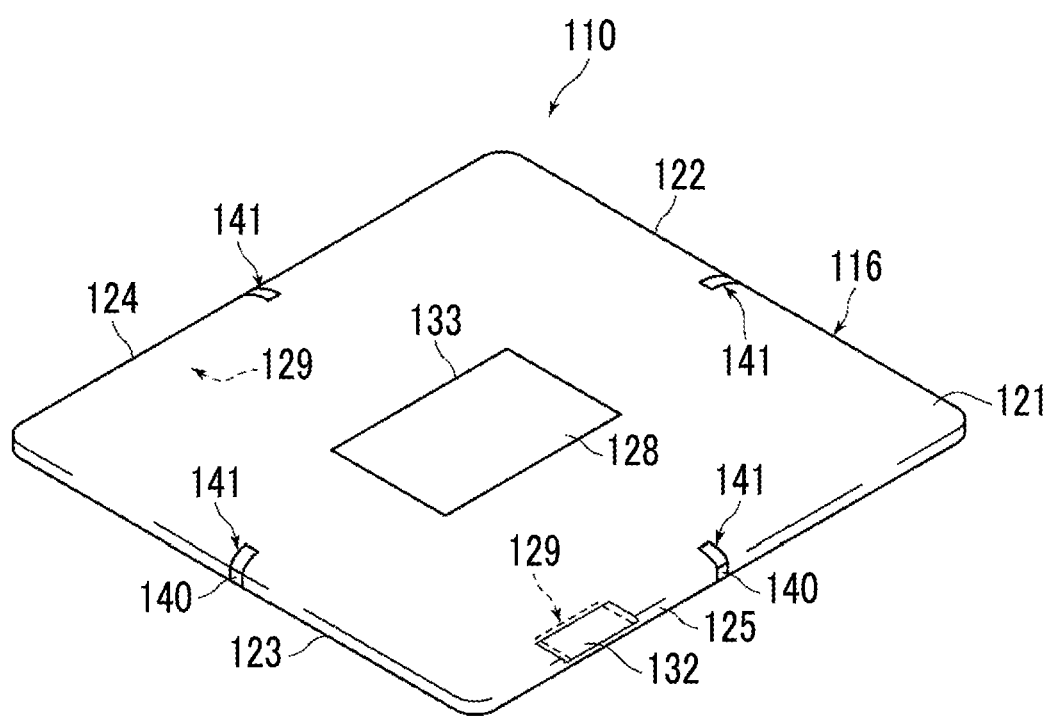
FIG. 15 is a perspective view showing the back side of the electronic cassette.

The electronic cassette 110 will be simply described here with reference to FIGS. 14 and 15. FIGS. 14 and 15 show the appearance of the electronic cassette 110 from the front side and the back side, respectively. The electronic cassette 110 of this example is used for, for example, medical radiography, and includes an image detection unit 115 that detects a transmitted X-ray image of the subject H on the basis of X-rays having been transmitted through the subject and a portable housing 116 that receives the image detection unit 115.

As well known, the image detection unit 115 includes a scintillator (phosphor) that converts incident X-rays into visible light and a thin-film-transistor (TFT) active matrix substrate. A rectangular imaging region in which a plurality of pixels for accumulating electric charges corresponding to visible light emitted from the scintillator are arranged is formed on the TFT active matrix substrate. A gate driver that applies gate pulses to a gate of a TFT to switch the TFT, a signal processing circuit that converts the electric charges accumulated in the pixels into voltage signals representing an X-ray image and outputs the voltage signals, a control unit that controls the drive of the gate driver and the signal processing circuit, and the like are built in the housing 116 in addition to the image detection unit 115.

The housing 116 has the shape of a rectangular parallelepiped composed of a front surface 120 on which X-rays are incident, a back surface 121 that faces the front surface 120, and four side surfaces 122, 123, 124, and 125. The housing 116 is made of, for example, a conductive resin and also functions as an electromagnetic shield that prevents the penetration of electromagnetic noise into the electronic cassette 110 and the emission of electromagnetic noise from the electronic cassette 110 to the outside. The housing 116 has substantially the same size as, for example, a film cassette or an imaging plate (IP) cassette and a computed radiography (CR) cassette that is based on International Organization for Standardization (ISO) 4090:2001.

A rectangular opening is formed on the front surface 120, and a transmissive plate 126 is mounted on the opening. A protective film (not shown) made of a resin, which transmits X-rays, is attached to the surface of the transmissive plate 126. Accordingly, the front surface 120 is a flat surface. The transmissive plate 126 has a planar size slightly larger than the planar size of the imaging region, and is made of a carbon material that is light and has a high stiffness and a high X-ray transmissivity.

The electronic cassette 110 includes a control device that controls the operation of the electronic cassette 110 and an antenna and an oscillation circuit that generate radio waves for the wireless communication of various kinds of information, such as X-ray images. In a case in which this wireless communication function is used, the electronic cassette 110 is driven by power to be supplied from a battery 128 and can be used in a so-called cableless form.

Further, the electronic cassette 110 includes a female connector 129 that communicates with a control device (not shown) by wire. A male connector 130 is connected to the female connector 129. One end of a cable 131, which is used for the wired connection between the electronic cassette 110 and the control device, is connected to the male connector 130. The other end of the cable 131 is connected to a connector (not shown) that is to be connected to the control device. The female connector 129 is covered and protected with a lid 132 in a case in which the male connector 130 is not connected, such as a case in which the wireless communication function is used, and the like.

The electronic cassette 110 receives not only various kinds of information supplied from the control device but also supplied power through the female connector 129. In a case in which the female connector 129 and the male connector 130 are connected to each other, the electronic cassette 110 is driven by power to be supplied from the control device. Furthermore, the battery 128 can also be charged with power to be supplied from the control device.

A battery-mounting portion 133 is provided at the central portion of the back surface 121. The battery 128, which supplies power used to drive the electronic cassette 110, is detachably mounted in the battery-mounting portion 133. FIG. 15 shows a state in which the battery 128 is mounted in the battery-mounting portion 133.

The battery-mounting portion 133 is a recess that is recessed toward the front surface 120 from the back surface 121. The battery-mounting portion 133 is formed to have the same shape and size as the planar shape and the planar size of the battery 128 so that the battery 128 is received substantially without a gap. The depth of the battery-mounting portion 133 from the back surface 121 is also substantially the same as the thickness of the battery 128. For this reason, in a state shown in FIG. 15 in which the battery 128 is mounted in the battery-mounting portion 133, the upper surface of the battery 128 is exposed from the back surface 121 and the upper surface of the battery 128 and the back surface 121 are flush with each other.

The electronic cassette 110 is provided with four marks 140 and four indicators 141 that are composed of, for example, light-emitting elements, such as LEDs or organic electro-luminescence (EL) elements. These marks 140 and these indicators 141 function to inform an operator of the position of the middle of each of sides of the rectangular imaging region.

After X-ray image information is recorded in the electronic cassette 110, the electronic cassette 110 is connected to an image recording device or an image display device for receiving voltage signals representing an X-ray image and the transmitted X-ray image of a subject H is recorded or reproduced and displayed on the basis of the signals.

Figure 13:
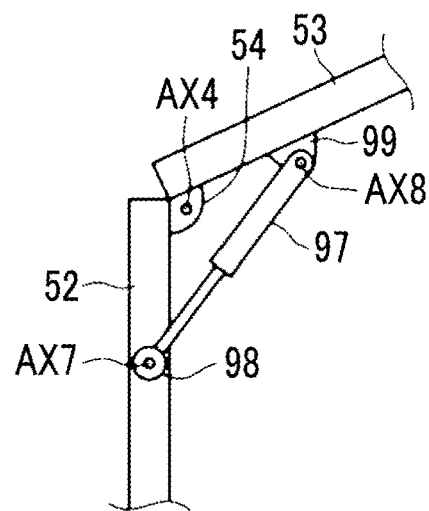
FIG. 13 is a side view showing another example of a radiation source support unit that can be applied to the radiographic imaging apparatus of the invention.

Here, it is preferable that it is the body-side arm 52 and the radiation source-side arm 53 of the arm unit 50 shown in FIG. 3 and the like are connected to each other by a gas spring 97 as shown in FIG. 13 so that the radiation source-side arm 53 is not lowered than a state in which the radiation source-side arm 53 is horizontal. Accordingly, in a case in which the radiation source 70 (see FIG. 3) held at the distal end portion of the radiation source-side arm 53 is disposed above the subject H and images the subject H, it is possible to avoid a situation that the radiation source-side arm 53 is carelessly lowered and the radiation source 70 bumps against the subject H.

The same elements of in FIG. 13 as the elements shown in FIGS. 1 to 12 having been previously described will be denoted by the same reference numerals as the reference numerals of FIGS. 1 to 12, and the description thereof will be omitted as long as the description thereof is not particularly needed (the same applies hereinafter). In the structure shown in FIG. 13, in detail, one end and the other end of a gas spring 97 are held at a holding portion 98 fixed to the body-side arm 52 and a holding portion 99 fixed to the radiation source-side arm 53 so as to be rotatable about rotation axes AX7 and AX8, respectively. In a case in which the body-side arm 52 and the radiation source-side arm 53 are to be received in the tubular member 51 shown in FIGS. 3 and 4, and the like, the holding portions 98 and 99 protruding from the respective arms 52 and 53 are positioned in the slit 51a of the tubular member 51. Accordingly, even though these protruding holding portions 98 and 99 are provided, the arms 52 and 53 can be received in the tubular member 51.

Figure 16:
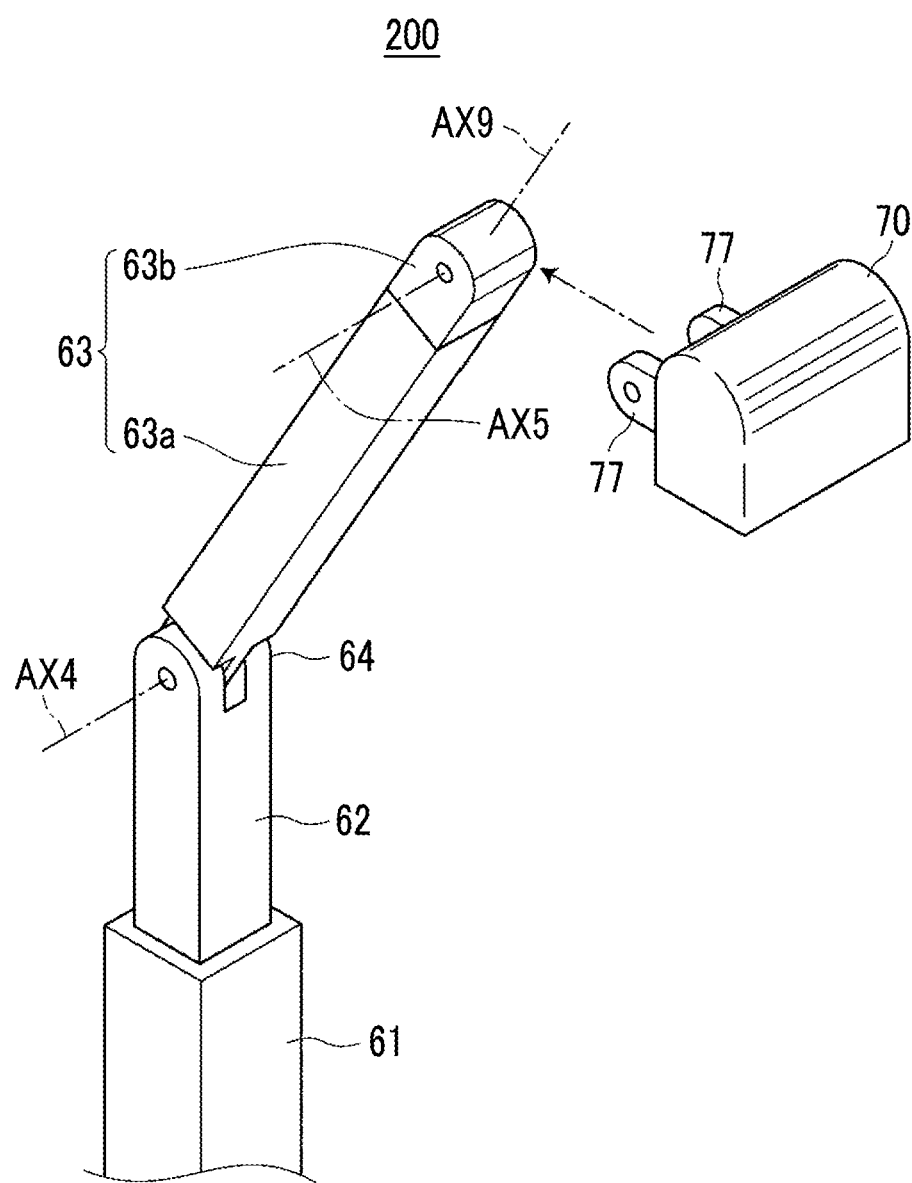
FIG. 16 is a perspective view showing still another example of the radiation source support unit that can be applied to the radiographic imaging apparatus of the invention.

Next, another example of the arm unit will be described with reference to FIG. 16. A body-side part of an arm unit 200 shown in FIG. 16 is composed of a tubular outer member 61 of which a proximal end is connected to, for example, the body unit 30 (see FIG. 2 and the like) and an inner member 62 which is received in the outer member 61 so as to be movable in an axial direction and a radiation source-side arm 63 is revolvably connected to a distal end side thereof. The radiation source-side arm 63 is connected to the inner member 62 through a connecting portion 64 so as to be revolvable about a revolution axis AX4. Further, the tubular outer member 61 is formed in, for example, a rectangular cylindrical shape.

The inner member 62 is received in the outer member 61 through an appropriate friction mechanism or through the above-mentioned gas spring. Accordingly, the inner member 62 is stopped in the outer member 61 at an arbitrary position in the axial direction, and can maintain the state thereof. Further, in a case in which the inner member 62 is received in the outer member 61 to a deep position, a part of the radiation source-side arm 63 also enters the outer member 61 in a state in which the longitudinal direction of the radiation source-side arm 63 is aligned with the longitudinal direction of the inner member 62. In a case in which a part of the radiation source-side arm 63 is received in the outer member 61 in this way, the radiation source-side arm 63 cannot revolve about the revolution axis AX4.

From the above, even in the case of the arm unit 200, the radiation source-side arm 63 cannot revolve in a state in which the body-side part of the arm unit formed of the outer member 61 and the inner member 62 is shorter than a predetermined length. That is, the outer member 61 forms revolution regulating unit in a case in which the length of the outer member 61 is set to the "predetermined length" in this structure. In this case, the length of the body-side part of the arm unit to be compared with the "predetermined length" is a length from the proximal end of the outer member 61 to the distal end of the inner member 62. For convenience sake, this rule is same even in a case in which the distal end of the inner member 62 is positioned in the outer member 61.

In the structure of FIG. 16, the outer member 61 of the body-side part of the arm unit is disposed so that the longitudinal direction of the outer member 61 is a direction perpendicular to the apparatus-placement surface 2 (see FIG. 2 and the like). Further, the radiation source-side arm 63 is composed of an elongated part 63a that is relatively long and a distal end part 63b that is connected to the distal end of the elongated part 63a and is relatively short. The distal end part 63b is connected to the elongated part 63a so as to be rotatable about a rotation axis AX9 parallel to the longitudinal direction of the radiation source-side arm 63. Furthermore, the radiation source 70 is connected to the distal end part 63b so as to be oscillatable about an oscillation axis AX5 in a state in which the distal end part 63b is interposed between two support members 77.

Since the radiation source 70, which is mounted on the radiation source-side arm 63 as described above, oscillates as described above and is rotatable about the rotation axis AX9 together with the distal end part 63b, the radiation source 70 is advantageous for the setting of a radiation-irradiation direction to various directions.

Figure 17:
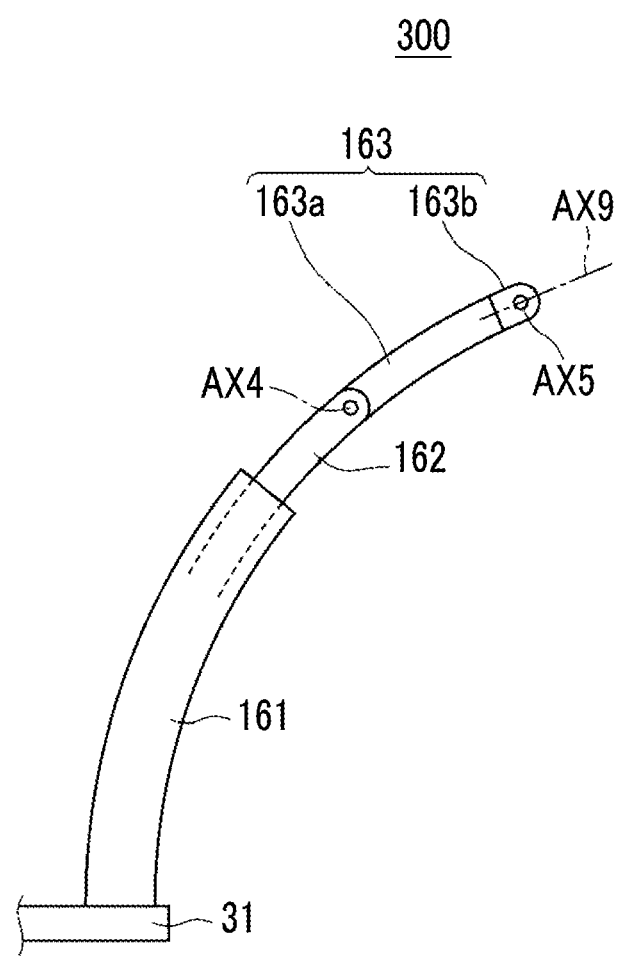
FIG. 17 is a side view showing yet another example of the radiation source support unit that can be applied to the radiographic imaging apparatus of the invention.

In the radiographic imaging apparatus of the invention, the arm unit may be formed in a curved shape. FIG. 17 is a side view showing an example of the arm unit that is formed in the curved shape. An arm unit 300 of FIG. 17 includes an outer member 161, an inner member 162, an elongated part 163a, and a distal end part 163b, which are formed to have the same structures as the outer member 61, the inner member 62, the elongated part 63a, and the distal end part 63b of the arm unit 200 of FIG. 16, except that the arm unit 300 is curved. Further, a radiation source-side arm 163 is composed of the elongated part 163a and the distal end part 163b. Furthermore, although not shown, a structure for mounting the radiation source 70 on the distal end part 163b is also the same as that of the arm unit 200 of FIG. 16.

Further, a structure in which the distal end part 163b is rotatable about a rotation axis AX9 parallel to the longitudinal direction of the radiation source-side arm 163 is also the same as that of the arm unit 200 of FIG. 16. More exactly, "the longitudinal direction of the radiation source-side arm 163" in this case is the tangential direction of an end portion, which is mounted on the radiation source, of the curved arm. Furthermore, in a case in which the radiation source is mounted on the arm through an object not having a "longitudinal" direction, for example, a spherical joint or the like, the longitudinal direction of the object is prescribed except for the arm.

It is preferable that the radiographic imaging apparatus of the invention is further provided with a height adjustment mechanism that can adjust a height to the radiation source support unit from the wheel unit. An embodiment of the radiographic imaging apparatus, which is provided with such a height adjustment mechanism, will be described below.

Figure 18:
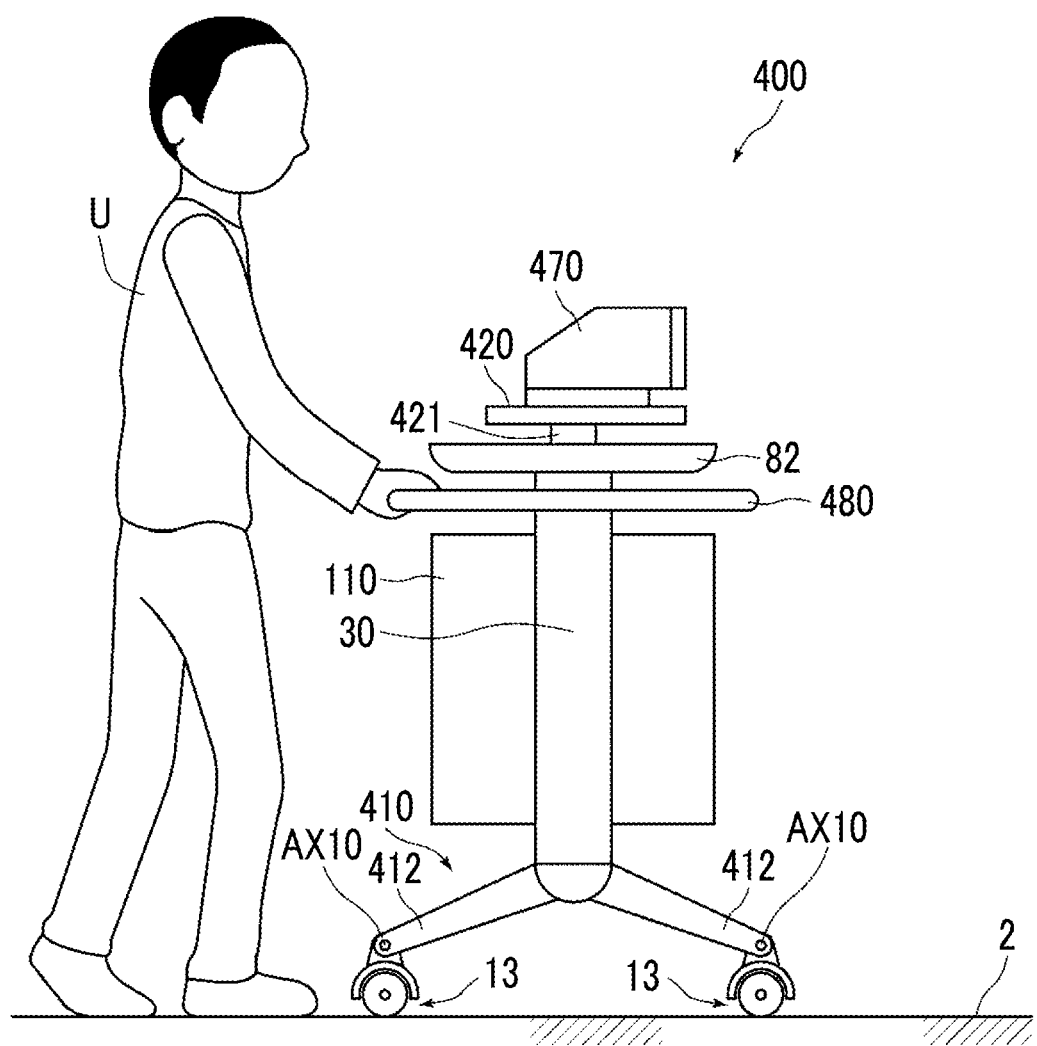
FIG. 18 is a side view of a radiographic imaging apparatus according to another embodiment of the invention.

A radiographic imaging apparatus 400 shown in FIG. 18 includes a leg unit 410, a body unit 30 that is held on the leg unit 410, a handle 480 that is used to push or pull the radiographic imaging apparatus 400, a console 82, a radiation source 470, a support base 420 that supports the radiation source 470, and a lifting mechanism 421 of which an upper end is fixed to the support base 420 and which can raise and lower the support base 420 with respect to the body unit 30. An electronic cassette 110 is detachably held on the body unit 30.

The body unit 30 and the console 82 are basically the same as those shown in FIG. 1. Further, the electronic cassette 110 is also basically the same as the already described electronic cassette. However, the electronic cassette 110 is held on the body unit 30 in this embodiment so that the direction of the electronic cassette 110 is different from the direction of the electronic cassette 110 of the radiographic imaging apparatus 1 of FIG. 1. The support base 420 is a radiation source support unit of this embodiment, and the radiation source 470 is mounted on the support base 420 so as to emit radiation in the lateral direction.

The leg unit 410 is composed of four legs 412 (of which only two legs are shown in FIG. 18) and wheel units 13 that are mounted on the lower ends of the respective legs 412. The wheel unit 13 is basically the same as that shown in FIG. 1, but is mounted on the leg 412 so as to be oscillatable about an oscillation axis AX10 here. The four legs 412 interlock with each other and are adapted so that an angle between each leg and the horizontal direction is adjustable. These legs 412 are adapted so that the oscillating position of the leg can be fixed by a fixing lever (not shown) or the like in a state in which the angle is arbitrarily adjusted.

The radiographic imaging apparatus 400 of this embodiment having the above-mentioned structure is adapted to be capable of traveling or moving on the apparatus-placement surface 2 in a case in which a user U of the apparatus grips the handle 480 and pushes or pulls the radiographic imaging apparatus. In a case in which the radiographic imaging apparatus 400 is to be moved in this way, the lifting mechanism 421 is in a state in which the lifting mechanism 421 is lowered to, for example, the lowest position.

Figure 19:
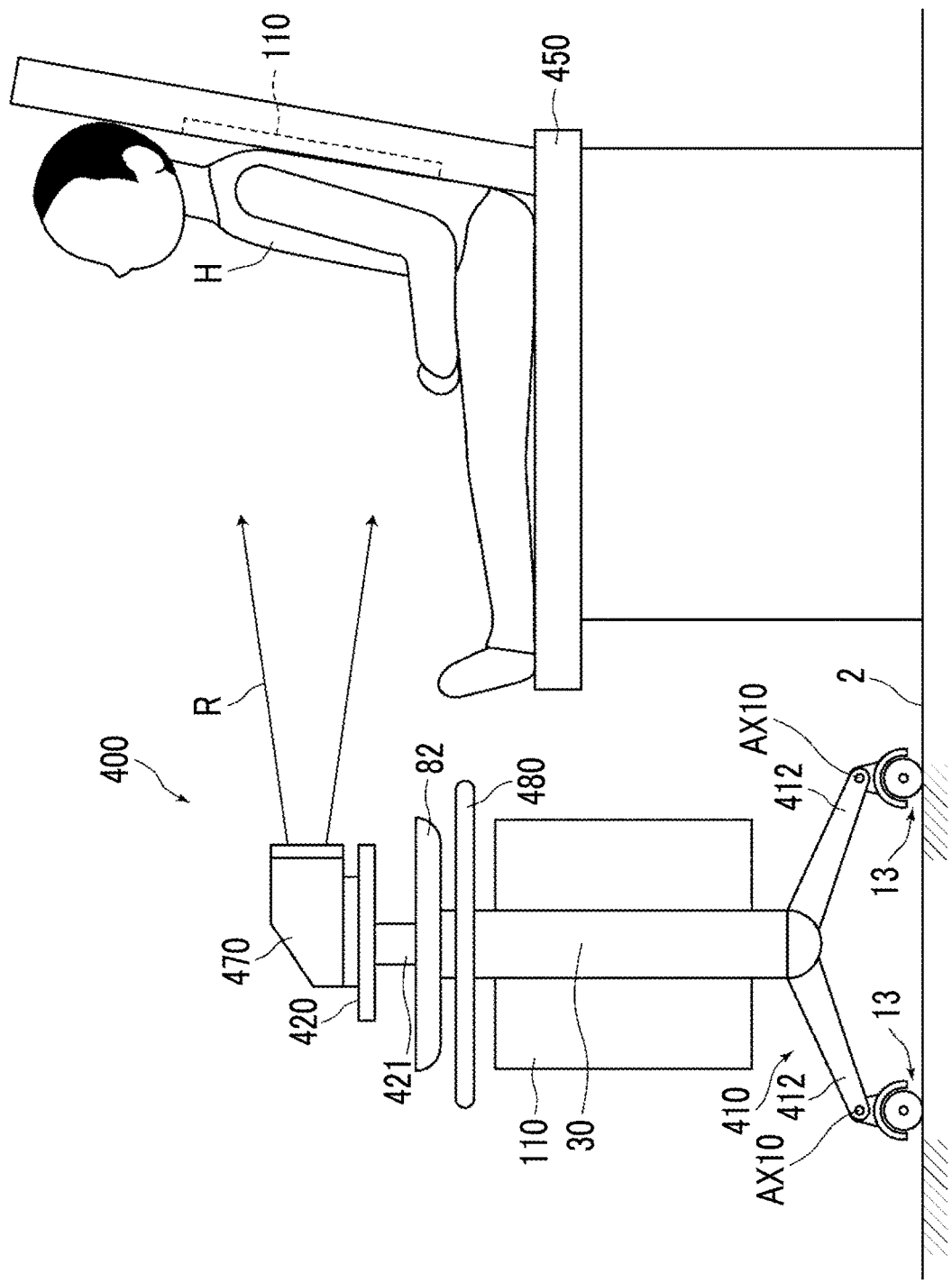
FIG. 19 is a side view showing an example of a state in which the radiographic imaging apparatus of FIG. 18 is in use.

The radiographic imaging apparatus 400 is used to take the image of the upright chest of a subject H, who is seated on an imaging table 450 as shown in, for example, FIG. 19, in an emergency medical facility or the like. That is, in this case, radiation R emitted from the radiation source 470 in the lateral direction is transmitted through the subject and the transmitted radiation image of the subject H formed by the radiation R is taken and recorded in the electronic cassette 110. In a case in which a radiation image is to be taken, the lifting mechanism 421 is raised by an appropriate distance so that the radiation source 470 is set to a position optimum for the height position of the subject H.

Figure 20:
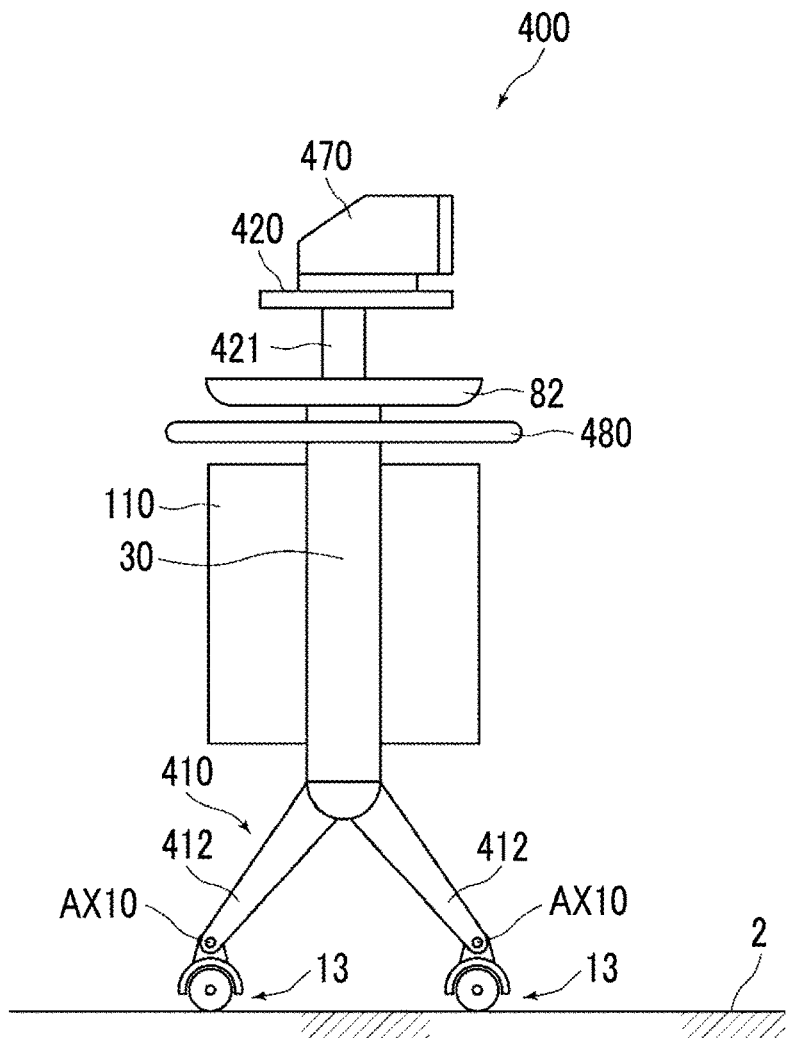
FIG. 20 is a side view showing another example of the state in which the radiographic imaging apparatus of FIG. 18 is in use.

In a case in which the radiation source 470 is required to be set to a higher position, the angles of the four legs 412 are changed in a direction where the lower ends of the respective legs approach each other as shown in FIG. 20. Accordingly, a height to the support base 420 from the wheel unit 13 is further increased, so that the radiation source 470 is set to a higher position. In a case in which the user U of the apparatus pushes or pulls the radiographic imaging apparatus 400 to moves the radiographic imaging apparatus 400 in addition to a case in which the user changes the height position of the radiation source 470, the radiographic imaging apparatus 400 of this embodiment can change the angle of each of the four legs 412 and change a height to the handle 480 from the wheel unit 13 so that the user easily performs such a work in accordance with the height of the user U of the apparatus.

As described above, in this embodiment, two mechanisms, that is, the four legs 412 of which angles with respect to the horizontal direction are changeable and the lifting mechanism 421 have been applied as the height adjustment mechanism that changes a height to the support base 420 from each wheel unit 13. However, only one of the two mechanisms may be applied. Further, in a case in which the radiation source 470 is mounted on the support base 420 so as to emit radiation R downward after a lifting mechanism having a relatively long lifting stroke is applied as the lifting mechanism 421, the image of the chest or the abdomen of a subject who lies down can also be taken. In that case, a source image distance (SID) between the radiation source and a radiation detector can also be set to a desired value by the operation of the height adjustment mechanism.

Figure 21:
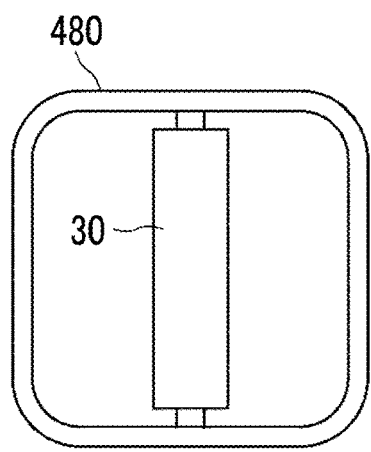
FIG. 21 is a plan view showing a part of the radiographic imaging apparatus of FIG. 18.

Here, FIG. 21 shows the planar shape of the handle 480. As shown in FIG. 21, in this embodiment, the handle 480 is formed in a shape where the handle 480 surrounds the body unit 30 over the entire circumference. Since the radiographic imaging apparatus 400 can be pushed or pulled from any side of the front, rear, left, and right sides of the body unit 30 in a case in which the handle 480 is formed in such a shape, the operability and mobility of the radiographic imaging apparatus 400 are more improved.

Figure 22:
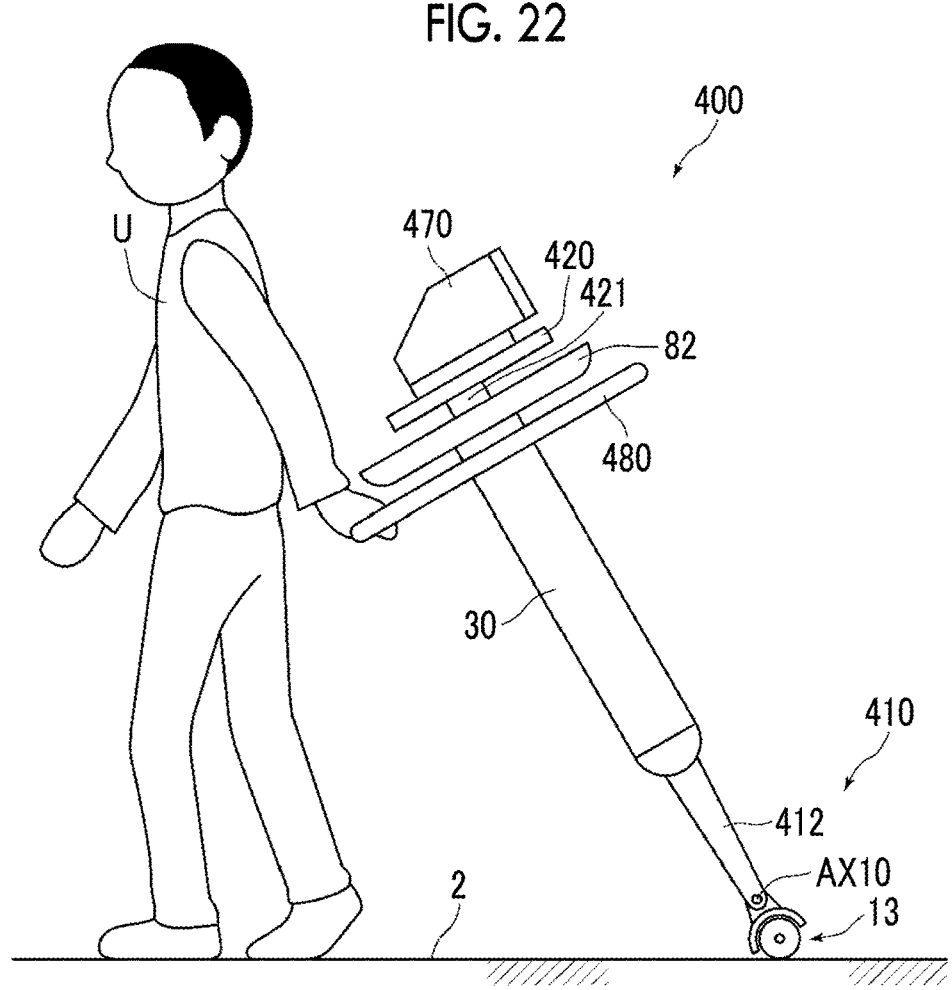
FIG. 22 is a side view showing a modification example of the radiographic imaging apparatus of FIG. 18.

In a case in which the four legs 412 are adapted so that an angle between each leg and the horizontal direction is changeable as described above, these legs 412 may be shifted from each other in the lateral direction not to interfere with each other and may be adapted so that the angle is changeable in a state in which all the legs 412 are aligned with each other as shown in FIG. 22. In such a case, it is easy to make the radiographic imaging apparatus 400 to travel and move while pulling the radiographic imaging apparatus 400 so that the radiographic imaging apparatus 400 is inclined as a whole as shown in FIG. 22. FIG. 22 shows a state in which the electronic cassette 110 is not held on the body unit 30.

Figure 23:
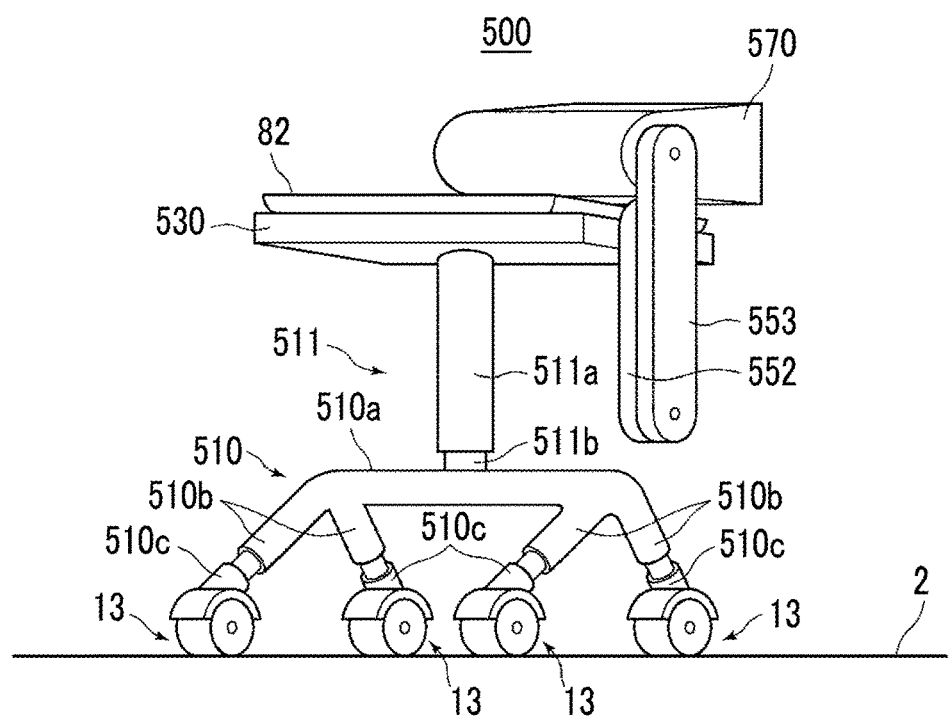
FIG. 23 is a perspective view of a radiographic imaging apparatus according to still another embodiment of the invention.

Next, another embodiment of the radiographic imaging apparatus including a height adjustment mechanism, which can adjust a height to the radiation source support unit from the wheel unit, will be described. A radiographic imaging apparatus 500 shown in FIG. 23 includes a lower leg part 510, an upper leg part 511 that is fixed onto the lower leg part 510, a body unit 530 that is held on the upper leg part 511, a console 82, a body-side arm 552 that is mounted on the body unit 530 through a hinge, a radiation source-side arm 553 that is mounted on the body-side arm 552 through a hinge, and a radiation source 570 that is mounted on the radiation source-side arm 553 through a hinge.

In this embodiment, the body unit 530 is a lateral body unit. Further, the body-side arm 552 and the radiation source-side arm 553 form a radiation source support unit of this embodiment. The lower leg part 510 and the upper leg part 511 form a leg unit of this embodiment together with wheel units 13 that are mounted on lower ends of the lower leg part 510.

The lower leg part 510 is composed of a connecting portion 510*a* that extends in the lateral direction, four lower outer tubes 510*b* that are obliquely connected to the connecting portion 510*a*, and lower inner tubes 510*c* that are inserted into the lower outer tubes 510*b*, respectively. The upper leg part 511 is composed of an upper outer tube 511*a* and an upper inner tube 511*b* that is inserted into the upper outer tube 511*a*. The lower end of the upper inner tube 511*b* is fixed to the connecting portion 510*a*. Further, the wheel unit 13 is mounted on the lower end of each lower inner tube 510*c*. The body unit 530 is fixed to the upper end of the upper outer tube 511*a*.

Since the length of a portion of the upper inner tube 511*b*, which is inserted into the upper outer tube 511*a*, is adjustable, a telescopic tube mechanism is composed of both the tubes 511*a* and 511*b*. That is, in a case in which the length of a portion of the upper inner tube 511*b* inserted into the upper outer tube 511*a* is adjusted, the total length of the upper outer tube 511*a* and the upper inner tube 511*b* is increased or reduced. Further, since the length of a portion of the lower inner tube 510*c*, which is inserted into the lower outer tube 510*b*, is also adjustable, a telescopic tube mechanism is composed of both the tubes 510*b* and 510*c*. That is, in a case in which the length of a portion of the lower inner tube 510*c* inserted into the lower outer tube 510*b* is adjusted, the total length of the lower outer tube 510*b* and the lower inner tube 510*c* is increased or reduced.

Both the tubes 511*a* and 511*b* of the upper leg part 511 are connected to each other through, for example, the above-mentioned gas spring. Accordingly, the upper inner tube 511*b* is stopped in the upper outer tube 511*a* at an arbitrary position in the axial direction, and can maintain the state thereof. On the other hand, the position of each lower inner tube 510*c* of the lower leg part 510 in the lower outer tube 510*b* in the axial direction can be maintained by the tightening of, for example, a set screw.

Figure 24:
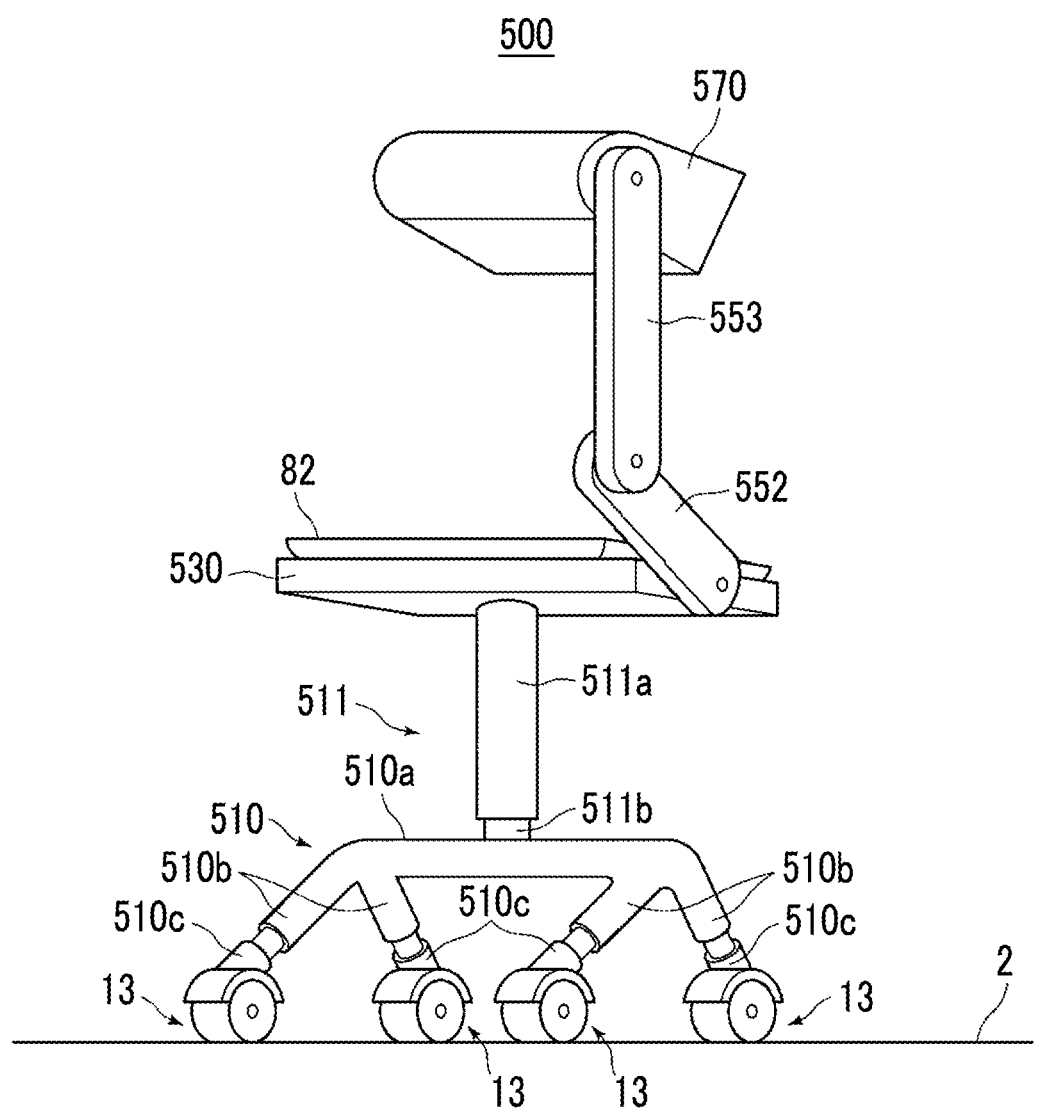
FIG. 24 is a perspective view showing an example of a state in which the radiographic imaging apparatus of FIG. 23 is in use.
Figure 25:
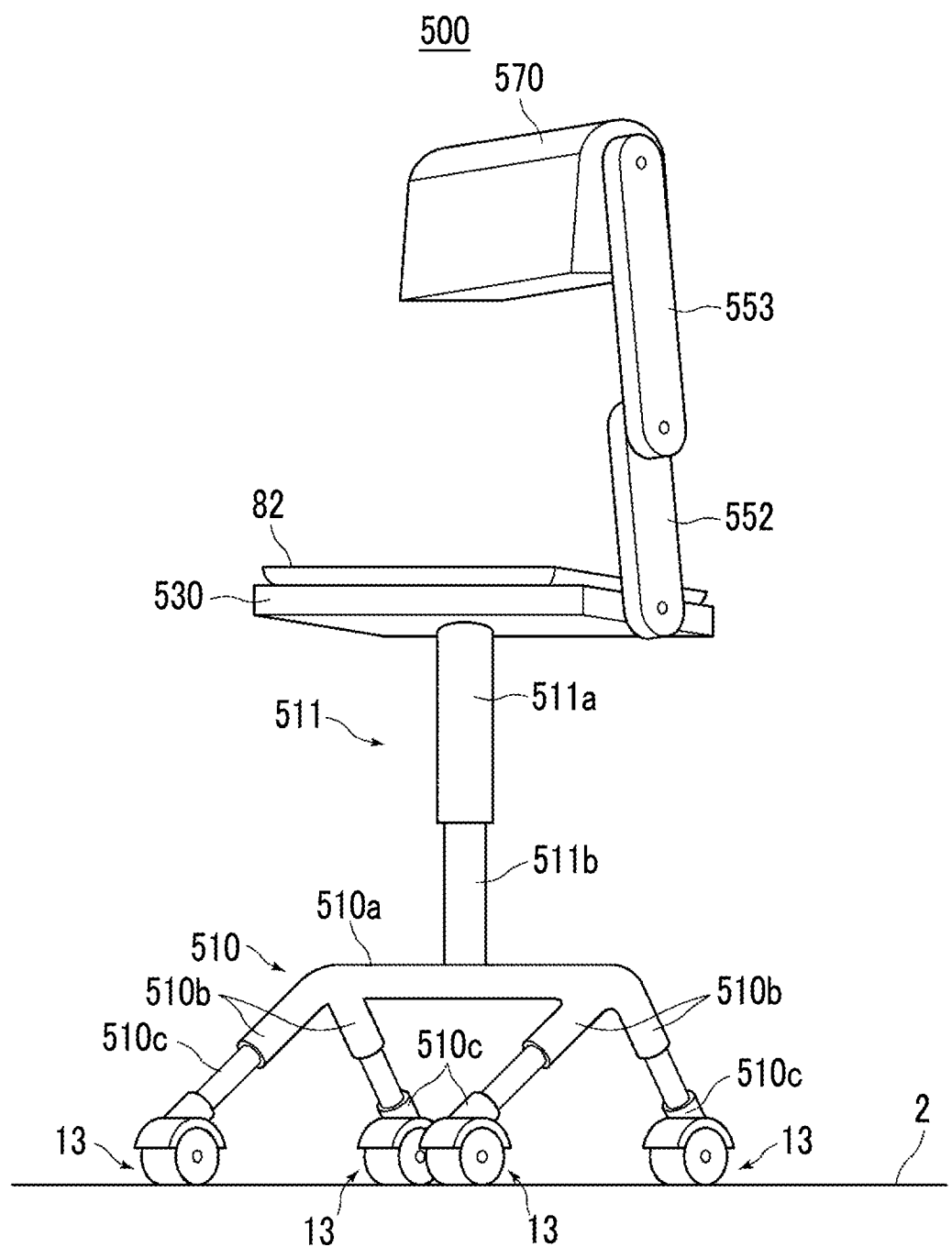
FIG. 25 is a perspective view showing another example of the state in which the radiographic imaging apparatus of FIG. 23 is in use.

In a case in which the radiographic imaging apparatus 500 of this embodiment having the above-mentioned structure is used, the body-side arm 552 and the radiation source-side arm 553 extend as shown in FIGS. 24 and 25 according to time and, for example, the radiation source 570 is set to a direction where radiation is emitted downward or in the lateral direction. In this case, the total length of the upper outer tube 511*a* and the upper inner tube 511*b* can be appropriately increased as shown in FIG. 25 to adjust the above-mentioned SID in a case in which radiation is emitted, for example, downward to take an image and to fit the height position of the radiation source 570 to the height of a subject in a case in which radiation is emitted, for example, in the lateral direction to take an image. Accordingly, the radiation source 570 can be set to a higher position. In addition, the total length of each lower outer tube 510*b* and each lower inner tube 510*c* can also be appropriately increased likewise as shown in FIG. 25 to set the radiation source 570 to a much higher position.

Figure 26:
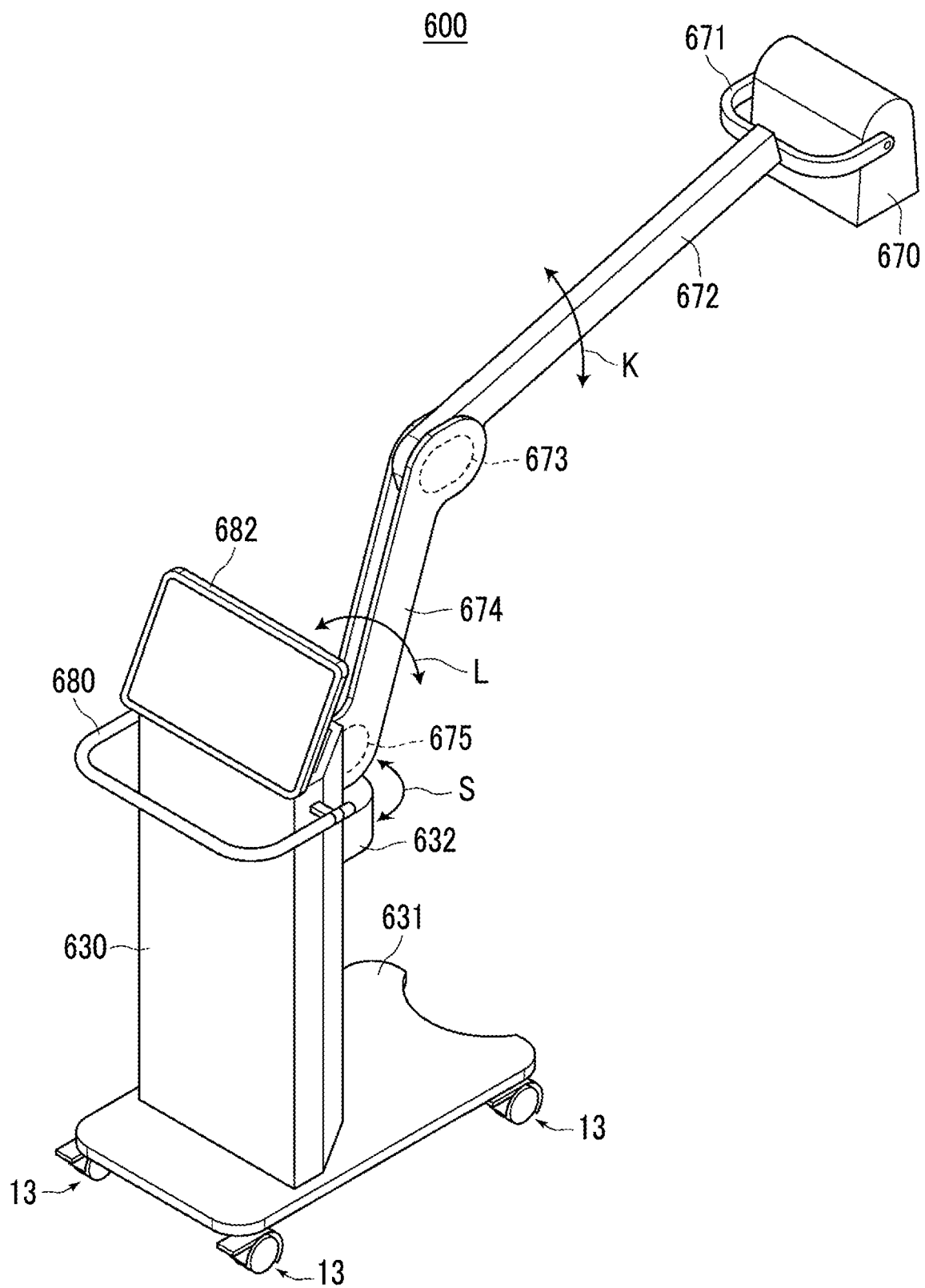
FIG. 26 is a perspective view of a radiographic imaging apparatus according to yet another embodiment of the invention.

Next, still another embodiment of the radiographic imaging apparatus including a height adjustment mechanism, which can adjust a height to the radiation source support unit from the wheel unit, will be described. A radiographic imaging apparatus 600 shown in FIG. 26 includes four wheel units 13 (of which only three wheel units are shown in FIG. 26), a base part 631 that forms a leg unit together with the wheel units 13, a body unit 630 that is fixed onto the base part 631, an arm support part 632 that is mounted on the body unit 630 through a lifting mechanism to be described later, a radiation source 670, a radiation source holding member 671 that holds the radiation source 670, a first arm 672 that supports the radiation source holding member 671, a second arm 674 of which a distal end is connected to a proximal end of the first arm 672 through a first joint 673, a second joint 675 that is connected to a proximal end of the second arm 674, and the arm support part 632 that supports the second arm 674.

The first arm 672 is adapted to be oscillatable with respect to the second arm 674 in the direction of arrow K by the action of the first joint 673. The second arm 674 is adapted to be oscillatable with respect to the arm support part 632 in the direction of arrow L by the action of the second joint 675. The first arm 672 and the second arm 674 are made to oscillate as described above, so that the height position of the radiation source 670 can be changed.

Further, the second joint 675 is mounted on the arm support part 632 so as to be rotatable in the direction of arrow S in a horizontal plane. Further, the arm support part 632 is connected to a lifting mechanism (not shown) that is disposed in the body unit 630.

Figure 27:
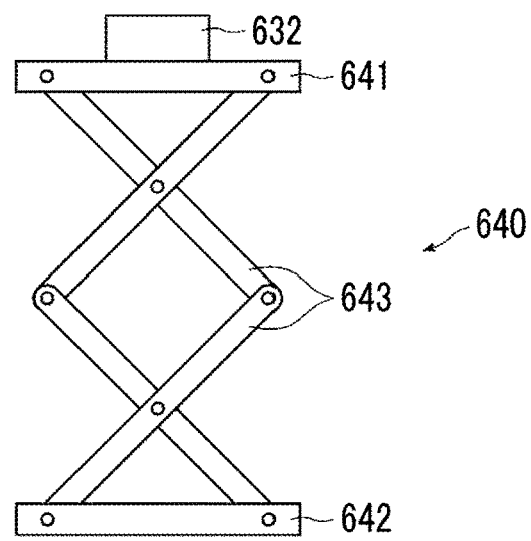
FIG. 27 is a front view of a mechanism that is a part of the radiographic imaging apparatus of FIG. 26.

The lifting mechanism will be described below with reference to FIG. 27. The lifting mechanism 640 is a pantograph type lifting mechanism as an example, and is composed of an upper end member 641 to which the arm support part 632 is connected, a lower end member 642 that is fixed to, for example, the above-mentioned base part 631 in the body unit 630, and a plurality of pantograph arms 643 that connect the upper end member 641 to the lower end member 642. The pantograph arms 643 of the lifting mechanism 640 are made to extend and retract, so that the vertical position of the upper end member 641, that is, the height position of the arm support part 632 connected to the upper end member 641 can be changed.

In a case in which the height position of the arm support part 632 is changed as described above, the height of the first arm 672 and the height of the second arm 674 are changed in FIG. 26 and the height position of the radiation source 670 is eventually changed. For example, in a case in which radiation is to be emitted downward from the radiation source 670 to take the image of the chest or the abdomen of a subject who lies down, the height position of the radiation source 670 is changed as described above, so that a distance SID (Source Image Distance) between the radiation source and the radiation detector can be set to a desired value. For example, the set screw for suppressing the movement of the upper end member 641 in the vertical direction is tightened, so that the height position of the arm support part 632 can be maintained at an arbitrary position.

Further, since the second joint 675 is mounted on the arm support part 632 so as to be rotatable in the direction of arrow S of FIG. 26 as described above in this embodiment, the first arm 672 and the second arm 674 can also be rotated in this direction to change the position of the radiation source 670.

Figure 28:
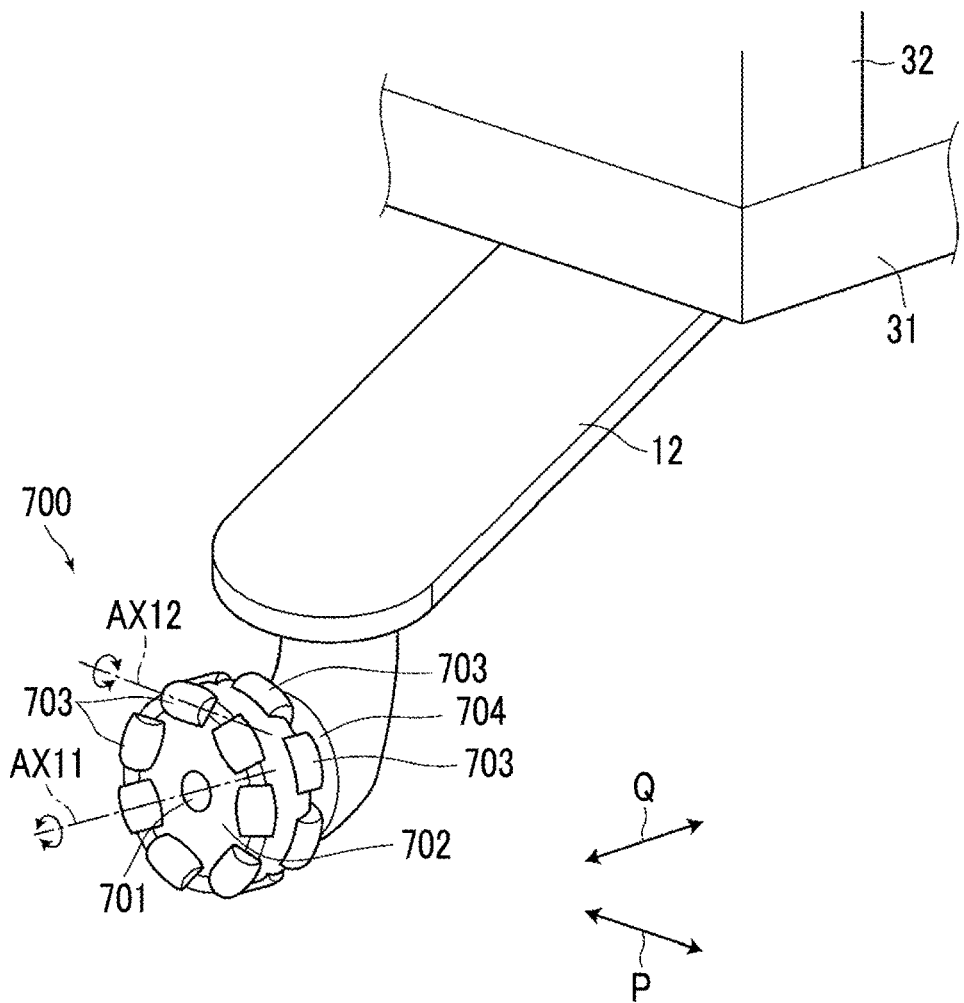
FIG. 28 is a perspective view showing another example of a wheel unit that can be applied to the radiographic imaging apparatus of the invention.

Next, another example of the wheel unit, which can be applied to the radiographic imaging apparatus of the invention, will be described with reference to FIG. 28. A wheel unit shown in FIG. 28 is composed of, for example, OMNI WHEEL (registered trademark). FIG. 28 shows a state in which the OMNI WHEEL 700 is mounted on the leg 12 of the radiographic imaging apparatus 1 shown in FIG. 1 as an example.

The OMNI WHEEL 700 is one of omnidirectionally moving wheels, and includes a rotating body 702 that is mounted on an axle 701 and is rotatable about a rotation axis AX11 in a normal direction and a reverse direction, and a plurality of rollers 703 that are mounted on the outer peripheral portion of the rotating body 702. For example, a barrel-shaped roller is applied as the roller 703.

In this example, seven rollers 703 are mounted on each of left and right sides of the rotating body 702, that is, a total of fourteen rollers 703 are mounted on the rotating body 702. Each of the seven rollers 703, which are mounted on one side of the left and right sides of the rotating body, is mounted on the rotating body 702 so as to be rotatable about a rotation axis AX12, which extends in a tangential direction of one circle coaxial with the rotation axis AX11, in a normal direction and a reverse direction. The same applies to the seven rollers 703 that are mounted on the other side of the left and right sides of the rotating body. Further, the seven rollers 703, which are mounted on one side of the left and right sides of the rotating body, are disposed at positions that face gaps between the seven rollers 703 that are mounted on the other side of the left and right sides of the rotating body. The OMNI WHEEL 700 having the above-mentioned structure is mounted on each leg 12 through a bearing part 704 receiving an axle 701.

In the case of the OMNI WHEEL 700, the rotating body 702 and the fourteen rollers 703 form one rotating wheel. That is, in a case in which a force acting in the direction of arrow P of FIG. 28 is applied to the radiographic imaging apparatus including the legs 12, each of the wheels, which is formed of the rotating body 702 and the rollers 703, rotates about the rotation axis AX11 while the fourteen rollers 703 serve as the outer peripheral surface of each wheel. Accordingly, the movement of the legs 12, that is, the radiographic imaging apparatus in the direction of arrow P is facilitated. Further, in a case in which a force acting in the direction of arrow Q of FIG. 28 is applied to the radiographic imaging apparatus including the legs 12, each of the grounded rollers 703 rotates about the rotation axis AX12. Accordingly, the movement of the legs 12, that is, the radiographic imaging apparatus in the direction of arrow Q is facilitated.

For example, a Mecanum wheel disclosed in JP2013-081659 can also be applied as the omnidirectionally moving wheel other than the above-mentioned OMNI WHEEL 700.

EXPLANATION OF REFERENCES 1, 400, 500, 600: radiographic imaging apparatus
2: apparatus-placement surface
10, 410: leg unit
12, 412: leg
13, 90: wheel unit
30, 530, 630: body unit
31: base part
32: housing
33: holding member
34: auxiliary leg
36: battery
37: DC power supply circuit
38: drive control circuit
39: inverter
50, 200, 300: arm unit
51: tubular member
52: body-side arm
53, 63: radiation source-side arm
54: revolution-holding mechanism
55: piston rod
61: outer member
62: inner member
63a: elongated part of radiation source-side arm
63b: distal end portion of radiation source-side arm
70, 470, 570, 670: radiation source
71, 77: support member
72: lock lever
82: console
97: gas spring
110: electronic cassette
420: support base
421: lifting mechanism
510: lower leg part
510b: lower outer tube 510c: lower inner tube
511a: upper outer tube
511b: upper inner tube
552: body-side arm
553: radiation source-side arm
631: base part
632: arm support part
640: lifting mechanism
671: radiation source holding member
672: first arm
673: first joint
674: second arm
675: second joint
700: OMNI WHEEL
AX1, AX9, AX11, AX12: rotation axis
AX2, AX4: revolution axis
AX3: axle
AX5, AX10: oscillation axis
AX6, AX7, AX8: rotation axis
H: subject
R: radiation
RC: radiation-emission axis

What is claimed is:

1. A radiographic imaging apparatus comprising:
a leg unit that includes three or more wheel units and is capable of traveling on an apparatus-placement surface;
a body unit that is held on the leg unit;
a radiation source support unit that is connected to the body unit;
a radiation source that is mounted on the radiation source support unit;
a battery that is received in the body unit and drives the radiation source; and
a circuit that is received in the body unit and controls the radiation source,
wherein at least one of the three or more wheel units comprises a revolving caster,
the body unit is adapted to be rotatable relative to the leg unit about a rotation axis extending in a vertical direction,
the radiation source support unit protrudes from the body unit in a horizontal direction, and
the body unit comprises a shape, where a length of the body unit in a direction parallel to the horizontal direction is shorter than a length of the body unit in a direction perpendicular to the horizontal direction in a plan view state.

2. The radiographic imaging apparatus according to claim 1,
wherein the body unit comprises a shape, where the length of the body unit in the direction parallel to the horizontal direction is equal to or shorter than 1/3 of the length of the body unit in the direction perpendicular to the horizontal direction in a plan view state.

3. The radiographic imaging apparatus according to claim 1,
wherein the body unit is inclined to a state in which an upper end of the body unit is closer to the radiation source than a lower end of the body unit.

4. The radiographic imaging apparatus according to claim 1,
wherein the body unit comprises a housing, where the battery and the circuit are received in the housing formed in a shape of a substantially rectangular parallelepiped.

5. The radiographic imaging apparatus according to claim 1,
wherein the circuit is divided into a plurality of blocks, and the plurality of blocks are arranged in a direction crossing the horizontal direction.

6. The radiographic imaging apparatus according to claim 1,
wherein in a case in which a circular locus, which is drawn by an outermost end of the leg unit in a case in which the leg unit revolves on the apparatus-placement surface so that at least two wheel units of the three or more wheel units follow a common circle, and the body unit are superimposed in a plan view state, the body unit is positioned inside the circular locus.

7. The radiographic imaging apparatus according to claim 1,
wherein the radiation source support unit is adapted to be extendable and retractable.

8. The radiographic imaging apparatus according to claim 1,
wherein the radiation source is adapted to be rotatable about an axis parallel to a longitudinal direction of a portion of the radiation source support unit on which the radiation source is mounted.

9. The radiographic imaging apparatus according to claim 1, wherein the radiation source is configured to oscillate to change an elevation angle of a radiation-emission axis, and the radiographic imaging apparatus further comprises:
an oscillating-position lock that fixes an oscillating position of the radiation source after the radiation source is positioned to a first elevation angle.

10. The radiographic imaging apparatus according to claim 9,
wherein the oscillating-position lock has a release position, and when the oscillating-position lock is in the release position, the radiation source moves to a lowered oscillating position at which the radiation-emission axis is lowered by a weight of the radiation source, the lowered oscillating position having a radiation-emission axis closer to vertical than when the radiation source is positioned to the first elevation angle.

11. The radiographic imaging apparatus according to claim 1,
wherein at least one of the three or more wheel units includes a brake unit.

12. The radiographic imaging apparatus according to claim 1, further comprising:
a height adjustment mechanism that is capable of adjusting a height to the radiation source support unit from at least one of the three or more wheel units.

13. The radiographic imaging apparatus according to claim 12,
wherein the height adjustment mechanism comprises the leg unit of which an angle with respect to the horizontal direction is adjustable.

14. The radiographic imaging apparatus according to claim 12,
wherein the height adjustment mechanism comprises a telescopic tube mechanism that is provided in at least a part of a gap between at least one of the three or more wheel units and the radiation source support unit.

15. The radiographic imaging apparatus according to claim 12,
wherein the height adjustment mechanism comprises a lifting mechanism that raises and lowers a portion of the body unit connected to the radiation source support unit.

16. A radiographic imaging apparatus comprising:
a leg unit that includes three or more wheel units and is capable of traveling on an apparatus-placement surface;
a body unit that is held on the leg unit;
a radiation source support unit that is connected to the body unit;
a radiation source that is mounted on the radiation source support unit;
a battery that is received in the body unit and drives the radiation source; and
a circuit that is received in the body unit and relates to a drive of the radiation source,
wherein at least one of the three or more the wheel units comprises:
an omnidirectionally moving wheel comprising a rotating body that rotates about a rotation axis, which is horizontal during travel, and
a plurality of rollers that are mounted on the rotating body along one circle coaxial with the rotating body, and
wherein the body unit is adapted to be rotatable relative to the leg unit about a rotation axis extending in a vertical direction,
the radiation source support unit protrudes from the body unit in a horizontal direction, and
the body unit is formed in a shape, where a length of the body unit in a direction parallel to the horizontal direction is shorter than a length of the body unit in a direction perpendicular to the horizontal direction in a plan view state.

17. The radiographic imaging apparatus according to claim 16,
wherein the body unit is inclined so that an upper end of the body unit is closer to the radiation source than a lower end of the body unit.

* * * * *